(12) United States Patent
Miyake et al.

(10) Patent No.: US 6,291,636 B1
(45) Date of Patent: Sep. 18, 2001

(54) MANUFACTURING METHOD OF ABSORBENT RESIN

(75) Inventors: Koji Miyake, Okayama; Toru Yanase, Hyogo; Yoshifumi Adachi, Himeji; Takumi Hatsuda, Takasago, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/285,877

(22) Filed: Apr. 7, 1999

(30) Foreign Application Priority Data

Apr. 7, 1998 (JP) .................................................. 10-094981

(51) Int. Cl.[7] ...................................................... C08F 6/00
(52) U.S. Cl. ............................................................. 528/502
(58) Field of Search ............................................. 528/502

(56) References Cited

U.S. PATENT DOCUMENTS

| | | |
|---|---|---|
| 5,118,719 | 6/1992 | Lind ........................................ 521/92 |
| 5,314,420 | 5/1994 | Smith et al. ............................ 521/64 |
| 5,328,935 | 7/1994 | Van Phan et al. ...................... 521/64 |
| 5,338,766 | 8/1994 | Phan et al. ............................. 521/63 |

FOREIGN PATENT DOCUMENTS

| | | |
|---|---|---|
| 0 497 623 A2 | 8/1992 | (EP) . |
| 0 508 810 A2 | 10/1992 | (EP) . |
| 0 744 435 A1 | 11/1996 | (EP) . |
| 0 811 636 A1 | 12/1997 | (EP) . |
| 08073518 | 3/1996 | (JP) . |
| WO 94/09043 | 4/1994 | (WO) . |

OTHER PUBLICATIONS

European Search Report, Communication dated Nov. 1, 2000.

Primary Examiner—Terressa M. Boykin
(74) Attorney, Agent, or Firm—Staas & Halsey LLP

(57) ABSTRACT

A manufacturing method of absorbent resin of the present invention includes, in addition to a drying step of drying hydrogel of a crosslinked polymer to obtain a dried product and a pulverizing step of pulverizing the dried product, a separating step of separating a incompletely dried product contained in the dried product therefrom. Since particles of the incompletely dried product are larger than those of the dried product, the former can be readily separated from the latter in the separating step by classifying the dried product to particles of a particle size within a predetermined range. Consequently, the incompletely dried product is never delivered to the pulverizing step, and therefore, it has become possible to prevent inconveniences, such as causing a trouble in pulverizing the dried product, and the incompletely dried product being mixed into the absorbent resin. Hence, in drying and subsequently pulverizing the hydrogel of a crosslinked polymer, that is, in manufacturing the absorbent resin, it has become possible to provide a method capable of manufacturing absorbent resin efficiently while avoiding troubles caused by the production of the incompletely dried product during the drying step.

32 Claims, 14 Drawing Sheets

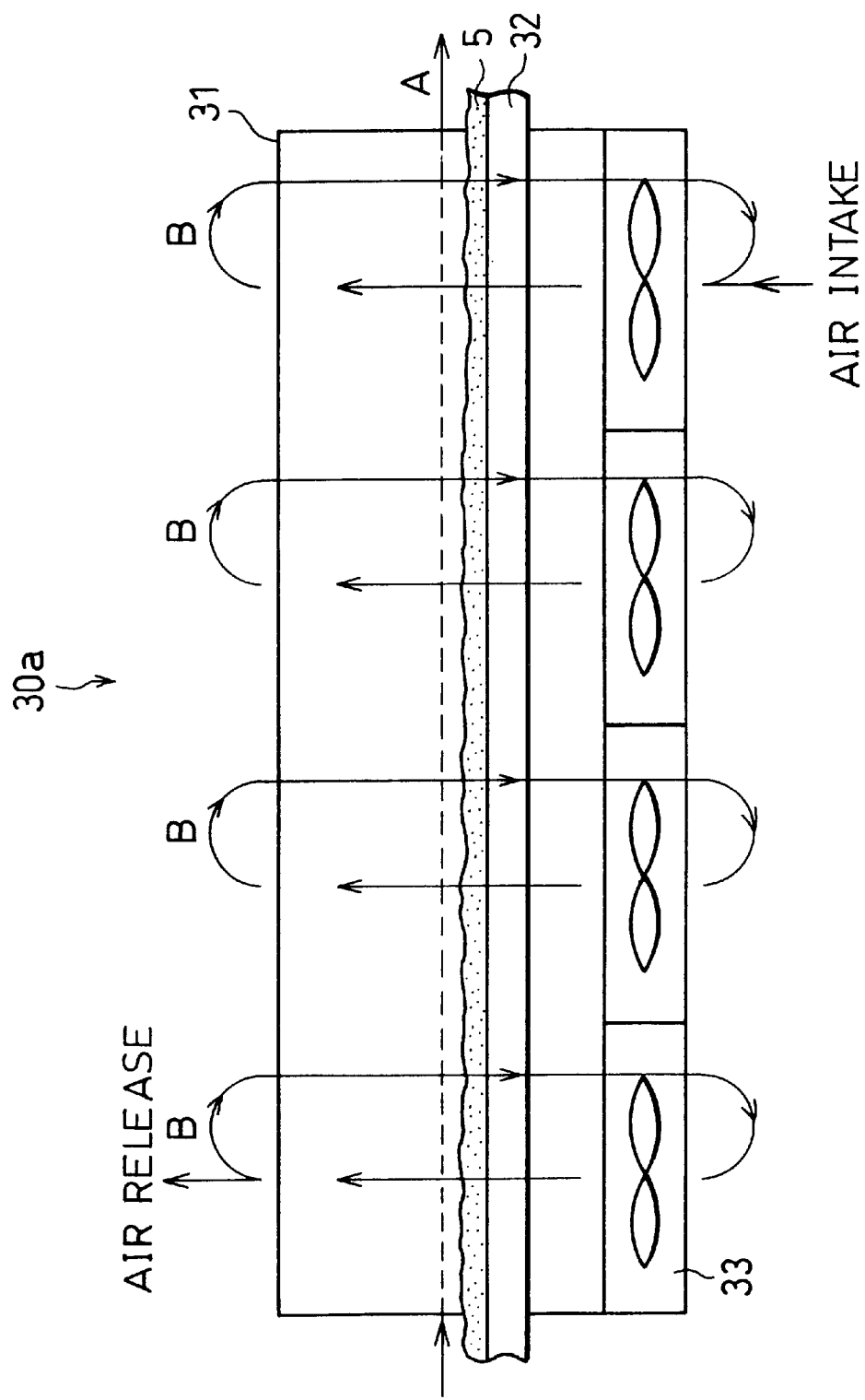

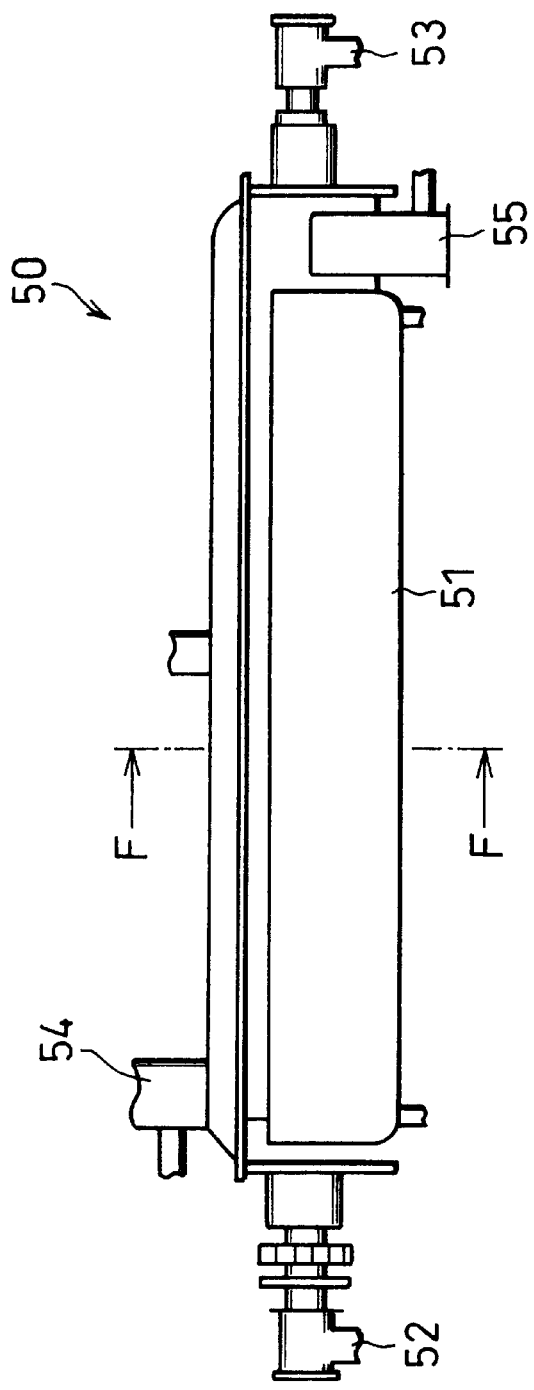
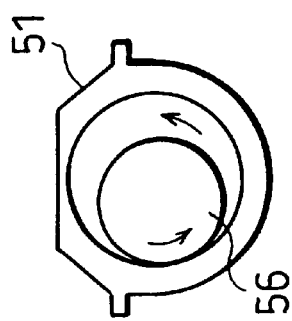
FIG. 8(a)
FIG. 8(b)

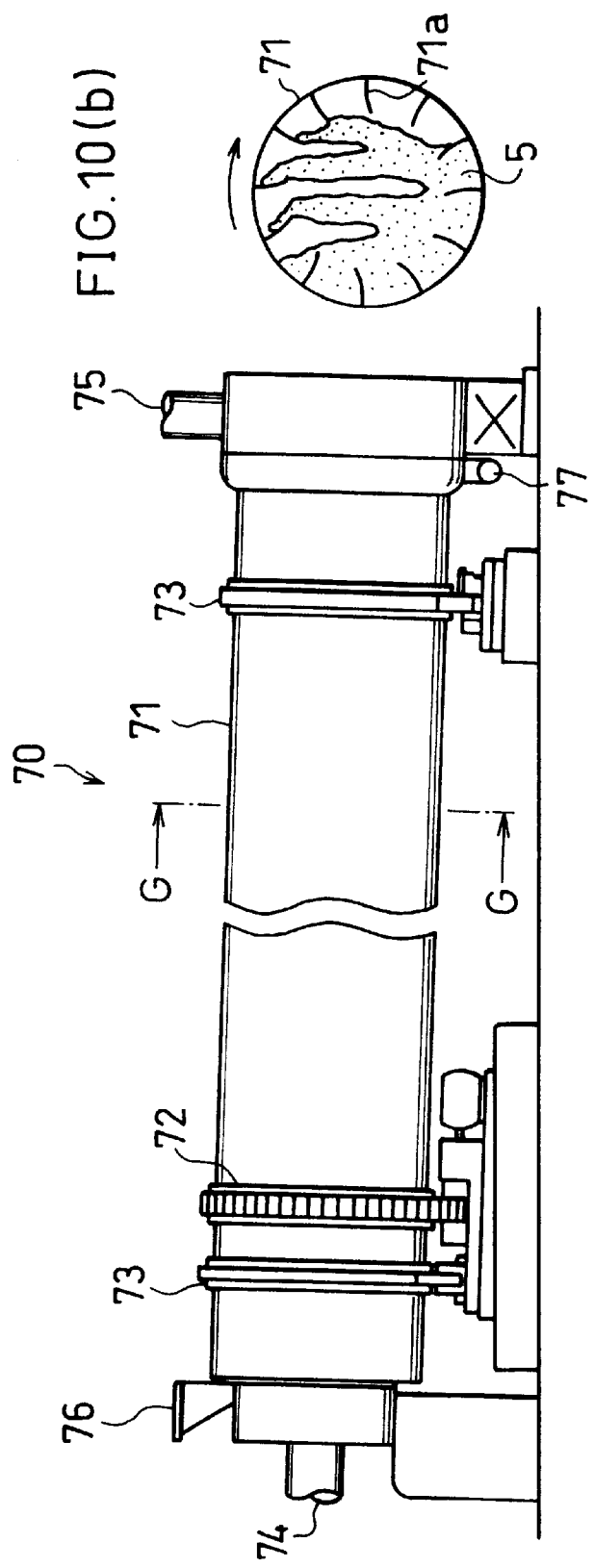

MANUFACTURING METHOD OF ABSORBENT RESIN

FIELD OF THE INVENTION

The present invention relates to a manufacturing method of absorbent resin having excellent absorbing rate and absorbing capacity by effectively drying and pulverizing aggregates of hydrogel of a crosslinked polymer having good viscosity and elasticity.

BACKGROUND OF THE INVENTION

It has been well known that hydrogel of a crosslinked polymer can be obtained as an absorbent crosslinked polymer by subjecting a water-soluble ethylenically unsaturated monomer to aqueous solution polymerization in the presence of a slight amount of a crosslinking agent.

The hydrogel of a crosslinked polymer (hereinafter, referred to simply as hydrogel) is a semi-solid gel substance having good elasticity. It is rare to use the hydrogel directly, and in most of the cases, it is divided to fine particles and dried. After the drying step, the hydrogel is pulverized adequately and made into a pulverized product of dry powder, so that it is used as absorbent resin, namely an absorbing agent. Methods of using a thin film dryer, a compartment tray dryer, a drum dryer, a band dryer, etc. are conventionally known as example drying methods adopted in the drying step.

To be more specific, the method using a band dryer is a method, in which hydrogel is placed on a belt conveyer or a screw conveyer equipped with an endless band made of a wire gauze or a porous plate, so that the hydrogel is dried with hot air blown to the same while it is conveyed through the dryer. This method using a band dryer is advantageous in that the hydrogel can be placed continuously without depending on the elasticity or strength of the hydrogel, and further in that a trouble caused when the hydrogel adheres to the dryer happens less frequently.

It is necessary to prevent as much as possible the hydrogel from being delivered to the subsequent pulverizing step before it is dried. The reason is as follows. That is, since incompletely dried hydrogel (hereinafter, referred to as incompletely dried product) is in the form of rubber having good viscosity, the incompletely dried product adheres to a pulverizer and often causes a trouble of stopping the pulverizer during the pulverizing step. Particularly, in case of pulverizing dried hydrogel to particles having a particle size of 1 mm or less, if the dried hydrogel contains the incompletely dried product, the incompletely dried product readily adheres to the pulverizer, and frequently causes a trouble of stopping the pulverizer.

Thus, in order to dry the hydrogel uniformly by the method using a band dryer, it is necessary to place the hydrogel on the band in a layer having a constant thickness. However, in practical applications, it is quite difficult to do so, and avoiding the production of the incompletely dried product is extremely difficult.

A technique disclosed in Japanese Laid-open Patent Application No. 73518/1996 (Japanese Official Gazette, Tokukaihei No. 8-73518, published on Mar. 19, 1996) is known as a method of reducing the production of the incompletely dried product. To be more specific, a pressure of hot air blown to the hydrogel and a pressure at a side opposing the hot-air-blowing side through the hydrogel are measured, so that a thickness of the hydrogel layer on the belt is detected in an on-time basis, according to which the operating conditions of the dryer are controlled. According to this technique, a thickness of the hydrogel layer on the band is measured in an on-time basis economically and effectively, and the operating conditions of the dryer are controlled adequately from time to time. Consequently, the hydrogel can be dried continuously and a dry product of the hydrogel containing a less amount of the incompletely dried product can be manufactured without using any special equipment.

However, the technique disclosed in the above publication can reduce the production of the incompletely dried product, but can not prevent the production of the incompletely dried product completely. Thus, no one has ever achieved a technique to effectively reduce the occurrence of troubles, such as stopping the pulverizer during the pulverizing step.

In other words, the operating conditions of the dryer can be controlled in detail by the method of the above publication, but this method can not prevent the production of the incompletely dried product by eliminating a basic cause because the hydrogel layer can not be maintained at a constant thickness.

To be more specific, in order to place a layer of the hydrogel on the band, aggregates of the hydrogel are often pulverized to fine particles. However, if the particle size of the fine particles of the hydrogel is 10 mm or greater, the incompletely dried product is readily produced, and the production of the same can not be prevented by merely setting the operating conditions of the dryer. Also, in the method using a band dryer, since a material subject to drying (hydrogel) is not stirred or a layer thereof is not turned over during the drying step, some specific portions of the material is hardly blown by hot air. Thus, also in this case, the production of the incompletely dried product can not be prevented by merely setting the operating conditions of the dryer.

Further, since absorbent capacity of the incompletely dried product is lower than that of the adequately dried product of the hydrogel, the physical properties of the resulting absorbent resin are deteriorated if the incompletely dried product is mixed into the dried product of the hydrogel in the pulverizing step.

The production of the incompletely dried product can be prevented completely by drying the hydrogel longer or at higher temperatures so as to eliminate the incompletely dried hydrogel (WO94/09043, published on Apr. 28, 1994). However, this method undesirably extends a drying time or increases operating energy of the dryer. Consequently, manufacturing efficiency of the dried product is deteriorated considerably and the manufacturing costs are increased markedly.

Moreover, according to this method, the hydrogel having been dried earlier is left under high temperature conditions with a slight amount of water until the incompletely dried hydrogel is dried. Thus, the hydrogel dried earlier may be dried exceedingly, thereby deteriorating the physical properties of the resulting absorbent resin.

As has been discussed, in drying the hydrogel, the conventional methods can prevent neither the production of the incompletely dried product completely nor deterioration of the physical properties of the dried product of the hydrogel obtained as the absorbent resin.

SUMMARY OF THE INVENTION

It is therefore an object of the present invention to provide a manufacturing method of absorbent resin having excellent absorbing rate and absorbing capacity by effectively drying and pulverizing aggregates of hydrogel of a crosslinked polymer (hereinafter, referred to simply as hydrogel) having good viscosity and elasticity.

The inventors of the present invention have been making efforts to solve the above problems, and on the assumption that a slight amount of incompletely dried hydrogel (hereinafter, referred to as incompletely dried product) is inevitably produced in the drying step of a manufacturing process of absorbent resin, they discovered that, by separating the incompletely dried product from the dried product, high-quality absorbent resin can be manufactured efficiently.

Also, the inventors achieved the present invention when they discovered that, in the manufacturing process of absorbent resin, since particles of the incompletely dried product in the powdery dried product of the hydrogel obtained after the drying step have larger volume and weight than those of the dried product, the incompletely dried product can be efficiently separated by classifying the powdery dried product.

In order to fulfill the above and other objects, a manufacturing method of absorbent resin of the present invention, having a drying step of drying the hydrogel to produce a dried product and a pulverizing step of pulverizing the dried product, is characterized by further having a separating step of separating a incompletely dried product contained in the dried product therefrom, which is conducted before or during the pulverizing step.

According to the above method, it has become possible to effectively prevent inconveniences caused when rubber of the incompletely dried product adheres to the pulverizer, such as stopping smooth pulverizing action by the pulverizer or stopping the operation of the pulverizer. Further, since the incompletely dried product is not mixed into the absorbent resin obtained as the final product, the deterioration of physical properties of the absorbent resin can be reduced, thereby making it possible to manufacture absorbent resin of a higher quality. In short, it has become possible to obtain high-quality absorbent resin efficiently while avoiding inconveniences caused upon production of the incompletely dried product.

In addition, the manufacturing method of absorbent resin of the present invention is further characterized in that the incompletely dried product is separated from the dried product in the separating step by classifying the dried product.

Generally, incompletely dried hydrogel (incompletely dried product) is in the form of rubber having good viscosity. Thus, it is not readily disintegrated and remains in the form of large particles. When the hydrogel is produced in the form of powdery particles, particles of the incompletely dried product are relatively large compared with those of the dried product because the former have higher water content and readily agglomerate. Consequently, powdery dried product contains particles of the dried product having a relatively small volume and particles of the incompletely dried product which were not pulverized and thereby having a large volume.

Thus, according to the above method, the larger particles of the incompletely dried product can be readily separated from the particles of the dried product by sifting (classifying) the powdery dried product through a sieve with a predetermined opening size or the like. Moreover, since the incompletely dried product can be separated from the dried product easily and efficiently without using any complex device, not only can high-quality absorbent resin be manufactured, but also an increase of the manufacturing costs can be suppressed.

The manufacturing method of absorbent resin of the present invention is further characterized in that a dryer used in the drying step is a band dryer, and that the manufacturing method further has a disintegrating step of roughly crushing aggregates of the dried product, which is conducted before or during the separating step.

According to the above method, absorbent resin can be mass-produced because the band dryer can dry the hydrogel continuously. When the band dryer is used, the hydrogel is dried and forms aggregates, but by disintegrating the aggregates in the disintegrating step, the dried product of the hydrogel can be mass-produced continuously. Moreover, by separating the incompletely dried product contained in the dried product from the same, the absorbent resin can be manufactured efficiently. Also, since the incompletely dried product is not mixed into the resulting absorbent resin, the quality of the same can be improved. Further, when the band dryer is used, not only can the hydrogel be placed continuously without depending on the elasticity or strength of the hydrogel, but also the frequency of troubles caused when the hydrogel adheres to the dryer can be reduced. Thus, the absorbent resin can be manufactured more efficiently and less expensively.

The manufacturing method of the absorbent resin of the present invention is further characterized in that the dried product is pulverized in the pulverizing step by a roll mill with at least one pair of rolls.

According to the above method, although the roll mill is relatively a simple device, it functions so sophisticatedly that it can pulverize a material subject to pulverization (the dried product of the hydrogel, herein) in a satisfactory manner. In particular, when the band dryer is used, the dried product can be pulverized continuously along with the drying action by the band dryer.

Also, the manufacturing method of the absorbent resin of the present invention is further characterized in that, a dryer used in the drying step is a pneumatic dryer equipped with a pulverizer which pulverizes the hydrogel to produce a pulverized product and a classifier which classifies the pulverized product.

According to the above method, the drying step, separating step, and pulverizing step can be conducted in a single phase. Hence, not only can the manufacturing efficiency of the absorbent resin be improved significantly, but also the manufacturing costs can be saved.

In addition, the manufacturing method of absorbent resin of the present invention is further characterized in that water content of the incompletely dried product exceeds 15 wt %.

When water content exceeds 15 wt %, the hydrogel turns into rubber gel exhibiting quite good viscosity and agglomerating property. On the other hand, when water content is 15 wt % or less, the hydrogel loses the viscosity and agglomerating property sharply, thereby turning into small particles.

According to the above method, the aforementioned property of the hydrogel is utilized to separate the incompletely dried product from the dried product. To be more specific, since the incompletely dried hydrogel (with water content exceeding 15 wt %) forms relatively large particles compared with those of the dried hydrogel (with water content of 15 wt % or less), the incompletely dried product can be readily separated from the dried product by sifting (classifying) the powdery dried product obtained after the drying step through a sieve or the like, or classifying the particles by a pneumatic dryer based on a particle size or a weight.

For a fuller understanding of the nature and advantages of the invention, reference should be made to the ensuing detailed description taken in conjunction with the accompanying drawings.

BRIEF DESCRIPTION OF THE DRAWINGS

FIG. 3 is a view explaining an arrangement of a parallel flow band-tunnel dryer used in the drying step of the manufacturing method of absorbent resin of the present invention;

FIG. 6 is a flowchart detailing a manufacturing process of absorbent resin of the present invention when any of the band dryers of FIGS. 2(a) and 2(b) and FIG. 3 is used;

FIG. 8(a) is a side view showing an arrangement of a stirring dryer equipped with a rotor used in the drying step of the manufacturing method of absorbent resin of the present invention;

FIG. 8(b) is a cross section of the stirring dryer taken on line F—F of FIG. 8(a);

FIG. 10(a) is a side view showing an arrangement of a rotary dryer used in the drying step of the manufacturing method of absorbent resin of the present invention;

FIG. 10(b) is a cross section of the rotary dryer taken on line G—G of FIG. 10(a);

DESCRIPTION OF THE EMBODIMENTS

Embodiment 1

Figure 1:
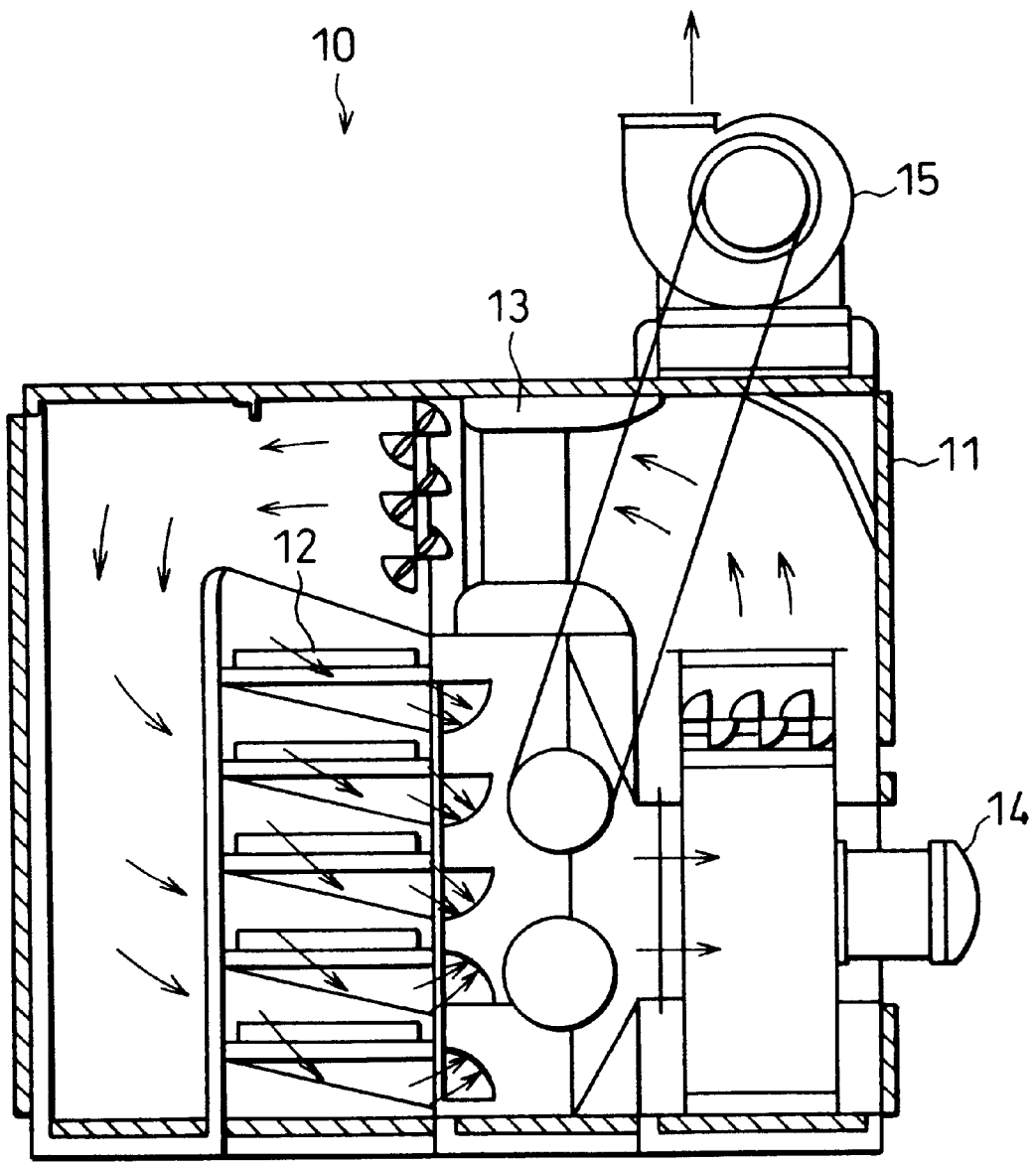
FIG. 1 is a view schematically showing an arrangement of a box-type dryer used in a drying step of a manufacturing method of absorbent resin in accordance with an example embodiment of the present invention.

Referring to FIGS. 1 through 6, the following description will describe an example embodiment of the present invention for purposes of explanation only, without any intention as a definition of the limits of the invention.

A manufacturing method of absorbent resin of the present invention is a method, wherein:

an ethylenically unsaturated monomer is subjected to aqueous solution polymerization in the presence of a slight amount of a crosslinking agent;

the resulting hydrogel of a crosslinked polymer is dried to produce a powdery dried product of the hydrogel of the crosslinked polymer;

a incompletely dried product contained in the dried product is separated from the same; and the dried product thus isolated is pulverized, whereby absorbent resin is manufactured as the final product.

The ethylenically unsaturated monomer used as a raw material of the hydrogel of the crosslinked polymer is not especially limited as long as it is a water-soluble monomer. Examples of the ethylenically unsaturated monomer include:

monomers containing acid groups, such as (meth)acrylic acid, β-acryloyloxy propionic acid, maleic acid, maleic anhydride, fumaric acid, crotonic acid, itaconic acid, cinnamic acid, 2-(meth)acryloylethane sulfonic acid, 2-(meth) acryloylpropane sulfonic acid, 2-(meth)acrylamide-2-methylpropane sulfonic acid, vinyl sulfonic acid, styrene sulfonic acid, allylsulfonic acid, vinyl phosphonic acid, 2-(meth)acryloyloxy ethyl phosphoric acid, and (meth) acryloxy alkane sulfonic acid, and alkali metal salts, alkali earth metal salts, ammonium salts, and alkylamine salts of these monomers;

dialkylaminoalkyl(meth)acryaltes, such as N,N-dimethylamino ethyl (meth)acrylate, N,N-dimethylamino propyl(meth)acrylate, and N,N-dimethylamino propyl (meth)acrylamide, and quaternary compounds of these compounds (for example, reaction products with alkylhydride and reaction products with dialkyl sulfuric acid);

dialkylaminohydroxyalkyl(meth)acryaltes and quaternary compounds thereof;

N-alkylvinylpyridinium halide;

hydroxyalkyl(meth)acrylates, such as hydroxymethyl (meth)acrylate, 2-hydroxyethyl(meth)acrylate, and 2-hydroxypropyl(meth)acrylate;

acrylamide, methacrylamide, N-ethyl(meth)acrylamide, N-n-propyl (meth)acrylamide, N-isopropyl(meth) acrylamide, N,N-dimethyl(meth)acrylamide;

alkoxy polyethylene glycol(meth)acrylate, such as methoxy polyethylene glycol(meth)acrylate;

polyethylene glycol mono(meth)acrylate;

vinyl pyridine, N-vinyl pyridine, N-vinyl pyrrolidone, N-acryloylpiperidine;

N-vinylacetoamide; etc.

One member or a mixture of two or more members selected from these examples can be used effectively as the ethylenically unsaturated monomer.

Of all these examples, monomers mainly composed of an acrylate monomer are more preferable than the others, because the resulting hydrogel of the crosslinked polymer has better absorbing property and safety. The acrylate monomer referred herein means acrylic acid and water-soluble salts thereof.

Examples of the water-soluble salts of acrylic acid include alkali metal salts, alkali earth metal salts, ammonium salts, hydroxy ammonium salts, amine salts, alkylamine salts of acrylic acid with a neutralization degree ranging from 30 to 100 mol %, and more preferably from 50 to 99 mol %. Of all these examples, sodium salts and potassium salts are particularly preferable. One member or a mixture of two or more members selected from these examples can be used effectively as the acrylate monomer.

The hydrogel of the crosslinked polymer can be obtained by polymerizing a monomer composition mainly composed of the ethylenically unsaturated monomer in the presence of a crosslinking agent. The monomer composition may include another kind of monomer (copolymerizible monomer) capable of copolymerizing with the ethylenically unsaturated monomer to the extent that a hydrophilic property of the resulting hydrogel of the crosslinked polymer is not deteriorated.

Examples of the copolymerizible monomer include: esters of (meth)acrylic acid, such as methyl(meth)acrylate, ethyl(meth)acrylate, and butyl(meth)acrylate;

hydrophobic monomers, such as vinyl acetate and vinyl propionate; etc.

One member or a mixture of two or more members selected from these examples can be used effectively as the copolymerizible monomer. Hereinafter, the monomer composition which may additionally include the copolymerizible monomer(s) is referred to as a monomer component.

Examples of the crosslinking agent used when polymerizing the monomer component include compounds having a plurality of vinyl groups in molecules, compounds having, in molecules, a plurality of functional groups reactive with carboxyl groups or sulfonic acid groups, etc. One member or a mixture of two or more members selected from these examples can be used effectively as the crosslinking agent.

Examples of compounds having a plurality of vinyl groups in molecules include N,N-methylenebis(meth) acrylamide, (poly)ethylene glycol di(meth)acrylate, (poly) propylene glycol di(meth)acrylate, trimethylolpropane tri (meth)acrylate, trimethylolpropane di(meth)acrylate, glycerin tri(meth)acrylate, glycerin acrylate methacrylate, ethyleneoxide denatured trimethylolpropane tri(meth) acrylate, pentaerythritol tetra(meth)acrylate, dipentaerythritol hexa(meth)acrylate, N,N-diallylacrylamide, triallylcyanurate, triallylisocyanurate, triallylphosphate, triallylamine, diallyloxy acetate, bis(N-vinylcarboxylic acid amido), tetra-allyloxyethane, etc.

Examples of compounds having, in molecules, a plurality of functional groups reactive with carboxyl groups or sulfonic acid groups include:

polyhydroxy alcohols, such as (poly)ethylene glycol, diethylene glycol, triethylene glycol, tetraethylene glycol, propylene glycol, dipropylene glycol, polypropylene glycol, 1,3-propanediol, 1,4-butanediol, 1,5-pentanediol, 1,6-hexanediol, 2,2,4-trimethyl-1,3-pentanediol, 2-butene-1,4-diol, (poly)glycerine, 1,2-cyclohexane dimethanol, 1,2-cyclohexanole, trimethylol propane, diethanol amine, triethanol amine, polyoxy propylene, an oxyethylene oxypropylene block copolymer, pentaerythritol, and sorbitol;

epoxy compounds, such as (poly)ethylene glycol diglycidyl ether, (poly)glycerol polyglycidyl ether, diglycerol polyglycidyl ether, (poly)propylene glycol diglycidyl ether, and glycidol;

polyvalent amine compounds, such as ethylene diamine, diethylene triamine, triethylene tetramine, tetraethylene pentamine, pentaethylene hexamine, polyamide polyamine, and polyethyleneimine, and condensates of these polyvalent amines and haloepoxy compounds;

polyvalent isocyanate compounds, such as 2,4-tolylene diisocyanate and hexamethylene diisocyanate;

polyvalent oxazoline compounds, such as 1,2-ethylene bisoxazoline;

silane coupling agents, such as γ-glycidoxy propyl trimethoxysilane, and γ-aminopropyl trimethoxysilane;

alkylene carbonate compounds, such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one;

halo epoxy compounds, such as epichlorohydrin;

hydroxides or chlorides of metals, such as zinc, calcium, magnesium, alminium, iron, and zirconium; etc.

A used amount of the crosslinking agent is not especially limited, but a preferable range is between 0.0001 and 10 mol %, and a more preferable range is between 0.001 and 1 mol % based on a total weight of the monomer component.

In the present invention, a method of polymerizing the monomer component is not especially limited, and known methods, such as bulk polymerization, precipitation polymerization, aqueous solution polymerization, and reversed-phase suspension polymerization, can be used. Of these methods, the aqueous solution polymerization using an aqueous solution of the monomer component is particularly preferable, because not only can the absorbing property of the resulting absorbent resin be improved, but also the polymerization can be readily controlled.

It is preferable to let the monomer component undergo polymerization without stirring. Further, when subjecting the ethylenically unsaturated monomer to the aqueous solution polymerization, either a continuous polymerization method or a batch polymerization method can be adopted. In addition, the polymerization can take place under atmospheric pressure, reduced pressure, or applied pressure. Note that it is preferable to conduct the polymerization reaction in an inert gas flow, such as nitrogen, helium, argon, and carbon dioxide.

At the beginning of the polymerization in the polymerization reaction, a polymerization initiator or activation energy rays, such as radiation rays, electron beams, UV rays, and electromagnetic beams, can be used. A radical polymerization initiator is often used as the polymerization initiator, examples of which include:

inorganic compounds, such as sodium persulfate, ammonium persulfate, potassium persulfate, and hydrogen peroxide;

organic peroxides, such as t-butyl hydroperoxide, benzoyl peroxide, cumene hydroperoxide;

azo compounds, such as 2,2'-azobis(N,N'-methyleneisobutyl amidine) and salts thereof, 2,2'-azobis (2-methylpropione amidine) and salts thereof, and 4,4'-azobis(4-cyanovalerianic acid); etc.

One member or a mixture of two or more members selected from these examples can be used effectively as the polymerization initiator. When peroxides are used as the polymerization initiator, redox polymerization can be conducted by additionally using a reducing agent, such as sulfite, bisulfite, and L-ascorbic acid.

In the present invention, it is particularly preferable that the hydrogel of the crosslinked polymer obtained by polymerizing the monomer component contains bubbles inside, because in this case, the resulting absorbent resin can attain better absorbing property. The hydrogel of the crosslinked polymer containing bubbles inside can be readily obtained by polymerizing the monomer component in the presence of the crosslinking agent in such a manner as to contain bubbles therein.

Here, known polymerization methods as follows can be used: a method of polymerizing the monomer component in the presence of an azo initiator; a polymerizing method which uses carbonate as a foaming agent (Japanese Laid-open Patent Application Nos. 237378/1993 and 185331/1995 (Japanese Official Gazettes, Tokukaihei Nos. 5-237378 and 7-185331) ); a polymerizing method which disperses a water-insoluble foaming agent, such as pentane and trifluoroethane, in the monomer (U.S. Pat. Nos. 5,328,935 and 5,338,766); a polymerizing method which uses a foaming agent in the form of solid microscopic particles (WO96/17884); a polymerizing method which polymerizes the monomer component in the presence of a surfactant while dispersing an inert gas; etc.

When polymerizing the monomer component in the presence of the crosslinking agent, it is preferable to use water as a solvent. In other words, it is preferable to use an aqueous solution of the monomer component and an aqueous solution of the crosslinking agent. This is because, in this case, not only can the absorbing property of the resulting absorbent resin be improved, but also the foaming agent can foam more efficiently.

Concentration of the monomer component in the above aqueous solution (hereinafter, referred to as monomer aqueous solution) is preferably in a range between 20 and 60 wt % based on a total weight of the monomer aqueous solution. When the concentration of the monomer component is below 20 wt %, an amount of water-soluble components in the resulting absorbent resin may undesirably increase, and an absorbing rate may not be improved because the foaming agent does not foam in a satisfactory manner. On the other hand, when the concentration of the monomer component exceeds 60 wt %, it may become difficult to control a reaction temperature and the foaming of the foaming agent.

A mixture of water and a water-soluble organic solvent may be used as the solvent for the monomer aqueous solution. Examples of such an organic solvent include: methyl alcohol, ethyl alcohol, acetone, dimethylsulfoxide, ethylene glycol monomethyl ether, glycerine, (poly)ethylene glycol, (poly)propylene glycol, alkylene carbonate, etc. One member or a mixture of two or more members selected from these examples can be used effectively as the organic solvent.

Compounds which can be dispersed or dissolved in the monomer aqueous solution are added as the foaming agent. Examples of the foaming agent include:

volatile organic compounds which can be dispersed or dissolved in the monomer aqueous solution, such as n-pentane, 2-methylpropane, 2,2-dimethylpropane, hexane, heptane, benzene, substituted benzene, chloromethane, chlorofluoromethane, 1,1,2-trichlorotrifluoroethane, methyl alcohol, ethyl alcohol, isopropyl alcohol, acetone, azodicarboneamide, and 2,2'-azobis isobutyronitrile;

carbonates, such as sodium bicarbonate, ammonium bicarbonate, ammonium carbonate, calcium carbonate, and basic magnesium carbonate;

ammonium nitrite;

dry ice;

acrylates of azo compounds containing amino groups; etc.

One member or a mixture of two or more members selected from these examples can be used effectively as the foaming agent.

A used amount of the foaming agent with respect to the monomer is not especially limited, and can be set adequately depending on a combination of the monomers and foaming agents. However, a preferable range with respect to 100 parts by weight of the monomer is in a range between 0.001 and 10 parts by weight. When a used amount of the foaming agent is outside of the above-specified range, the resulting absorbent resin may not attain satisfactory absorbing property.

The absorbent resin of the present invention is manufactured from the hydrogel of the crosslinked polymer (hereinafter, referred to simply as hydrogel) obtained in the above-explained manner. The manufacturing method of the absorbent resin of the present invention includes at least:

a drying step of drying the hydrogel until it attains a predetermined range of water content to produce a powdery dried product;

a pulverizing step of pulverizing the dried product to finer particles to obtain a final product (absorbent resin); and a separating step of separating the incompletely dried product of the hydrogel contained in the dried product from the same. Here, an average molecular weight (polymerization degree) of the absorbent resin is not especially limited.

The water content of the hydrogel before the drying step is preferably in a range between 20 and 80 wt %. When the water content is less than 20 wt %, it may become difficult to divide the hydrogel, or in case that the hydrogel contains bubbles, the bubbles may be burst. On the other hand, when the water content exceeds 80 wt %, it takes too long to dry the hydrogel.

After or during the polymerization, the hydrogel is divided by a kneader, a meat chopper, a Guillotine cutter, a cutting mill or the like. It is preferable that 90% or greater of the particles of the divided hydrogel have a particle size ranging from 0.1 to 10 mm. Also, it is preferable that an average particle size of the particles of the hydrogel is in a range between 0.5 and 5 mm, and more preferably, in a range between 0.8 and 4 mm. When the particle size or average particle size is outside of the above-specified ranges, the hydrogel may not be dried efficiently.

A dryer used in the drying step is not especially limited, and used in the present embodiment are the dryers in which the hydrogel agglomerates during the drying step (hereinafter, referred to as agglomerating dryer), such as a box-type dryer, a drum dryer, and band dryers including a parallel flow band-tunnel dryer and a through-flow band dryer. Dryers in which the hydrogel does not agglomerate during the drying step (hereinafter, referred to as non-agglomerating type dryers) can be also used suitably, but the description of which will be given in Embodiment 2 below.

The following will explain in detail an arrangement of the agglomerating dryer of each type and a manufacturing process of the absorbent resin of the present invention using the dryer of each type.

The box-type dryer includes a plurality of drying shelves in a box casing of a predetermined size, and a material subject to drying (hydrogel, herein) is dried by being allowed to stand on the drying shelves while hot air or the like is blown through.

The box-type dryer includes two models: one uses hot air for the drying and the other does not. As an example box-type dryer, FIG. 1 shows a box-type dryer 10 which dries the hydrogel by using hot air as through-flow. The box-type dryer 10 includes a casing 11, a plurality of drying shelves 12 in the casing 11, an air heater 13 which generates hot air, an air circulating fan 14 which circulates hot air, an air releasing fan 15 which release hot air, etc. With the box-type dryer 10, hot air is circulated in the casing 11 from the air heater 13 to the drying shelves 12 to the air circulating fan 14 and to the air heater 13 (indicated by arrows in the drawing), whereby the hydrogel on the drying shelves 12 are dried by the hot air.

Since the box-type dryer adopts the batch method, it is advantageous in that it can be suitably used to manufacture various kinds of products each in a small amount, and to dry a material like the hydrogel of the present invention, which forms particles or aggregates when dried. Moreover, since the costs can be cut, the manufacturing costs can be saved as well.

A parallel flow box-type dryer is also available as the model using hot air. Further, some other models of the box-type dryers do not use hot air, examples of which include a vacuum box-type dryer which vacuums the interior of the casing, a heat conducting box-type dryer, and a heat radiating box-type dryer. The drying method can be selected adequately depending on the properties of the hydrogel as the material subject to drying or the resulting absorbent resin.

The drum dryer dries a material subject to drying by forming a thin film of a liquid or mud of the material subject to drying on the surface of a rotating drum heated from the inside by a heating medium, such as vapor, while the rotating drum turns once. In case that the material subject to drying is in the form of a liquid, a layer of a thin film is formed on the rotating drum by dipping the rotating drum in the liquid, splashing the liquid by rotating blades, or spraying the liquid. In case that the hydrogel is in the form of mud like in the present invention, the hydrogel is often adhered to the rotating drum by another small roller.

Figure 2A:
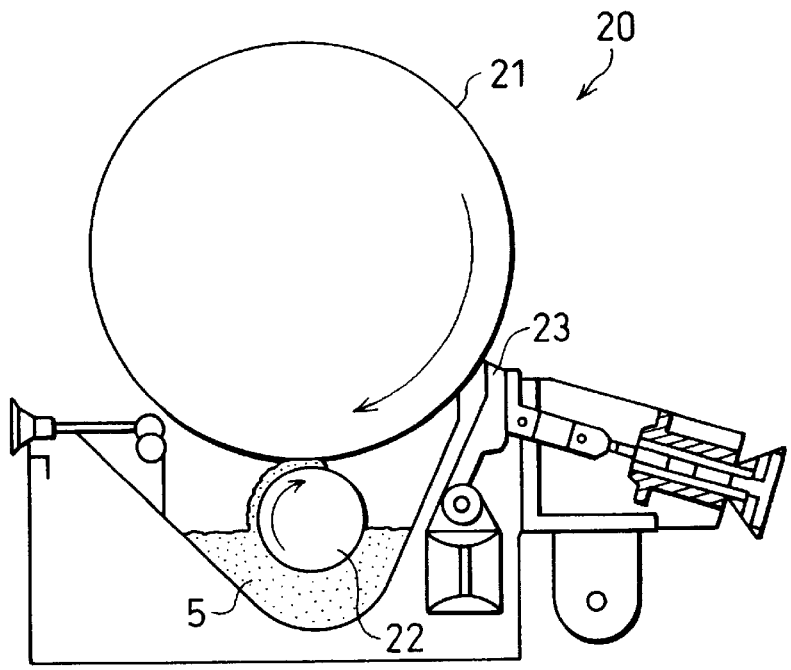
FIG. 2(a) is a view schematically showing an arrangement of a drum dryer used in a drying step of the manufacturing method of absorbent resin of the present invention.

For example, as shown in FIG. 2(a), a drum dryer 20 includes a rotating drum 21 which turns in a direction indicated by an arrow, a supplying roller 22 placed to oppose the rotating drum 21, a fixed knife 23 which separates a thin film of the dried product from the rotating drum 21, etc. The supplying roller 22 turns in a reversed direction to the turning direction of the rotating drum 21 (direction indicated by an arrow), whereby the hydrogel (mud of the material subject to drying) 5 is supplied to the rotating drum 21. The hydrogel 5 is dried while the rotating drum 21 turns once, and immediately separated therefrom by the fixed knife 23. Thus, the drum dryer 20 is advantageous in that the hydrogel 5 is never dried exceedingly.

Figure 2B:
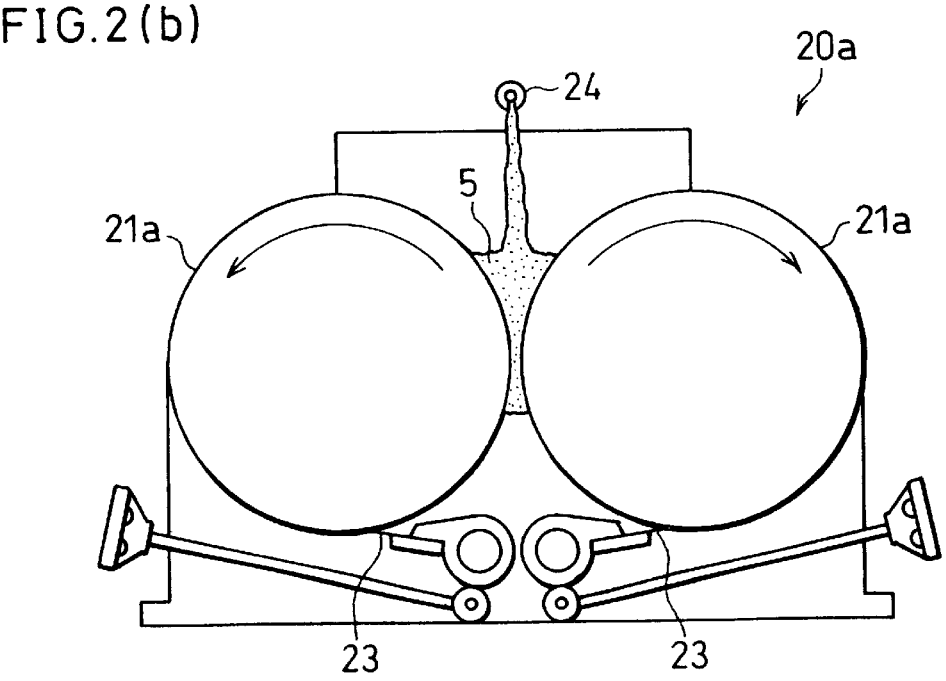
FIG. 2(b) is a view schematically showing another arrangement of the drum dryer used in the drying step of the manufacturing method of absorbent resin of the present invention.

Also, a drum dryer 20a shown in FIG. 2(b), which is equipped with two opposing rotating drums 21a, can be also used. The rotating drums 21a turn in opposite directions (directions indicated by their respective arrows). The drum dryer 20a is also equipped with a supplying section 24 of the hydrogel 5 placed above the rotating drums 21a, so that the hydrogel 5 is supplied to a space between the rotating drums 21a. As soon as the hydrogel 5 is dried, the dried product is broken up as it is drawn into the rotating drums 21a, and subsequently separated from the rotating drum 21a by the fixed knives 23. Thus, the drum dryer 20a is advantageous in that the drying and the disintegrating described below can be conducted simultaneously.

The drum dryer can attain heat efficiency as high as 80–90%, because the hydrogel is brought into contact to a heating medium through the rotating drum. Further, the drum dryer is generally advantageous in that the equipment costs and maintenance fees can be saved, and that it can be manipulated more flexibly. For example, the drum dryer can dry the hydrogel by either a batch method or a continuous method. The models of the drum dryer can be selected adequately depending on the properties of the hydrogel as the material subject to drying, or the resulting absorbent resin.

Unlike the above-explained box-type dryer, the band dryer dries a material subject to drying continuously. For example, the band dryer is equipped with an endless band having a width of 1–3 m made of a metal gauze or a porous plate, and the material subject to drying is placed on the band and dried as it is conveyed through the dryer. Generally, hot air is used for drying, and hot air is used as parallel flow or through-flow in most of the cases.

The band dryers using the parallel flow of hot air include a parallel flow band-tunnel dryer. As shown in FIG. 3, a parallel flow band-tunnel dryer 30a includes a tunnel drying chamber 31 and an endless band 32 in the drying chamber 31, which is driven in a direction indicated by an arrow A by an unillustrated driving device. The hydrogel 5 is placed on the band 32, and dried while it is conveyed along the direction indicated by the arrow A through hot air flowing in a direction (indicated by arrows B) that intersects at right angles with the band 32.

In order to prevent channeling of hot air, the parallel flow band-tunnel dryer 30a is arranged to generate cross flows of hot air, whereby hot air is flown throughout the drying chamber 31 in parallel and counter by fans 33. By continuously bringing hot air into contact with the hydrogel 5, the hydrogel 5 can be dried in a satisfactory manner. The parallel flow band-tunnel dryer 30a may be composed of a series of batches, so that air is supplied or released by each fan 33.

Figure 4A:
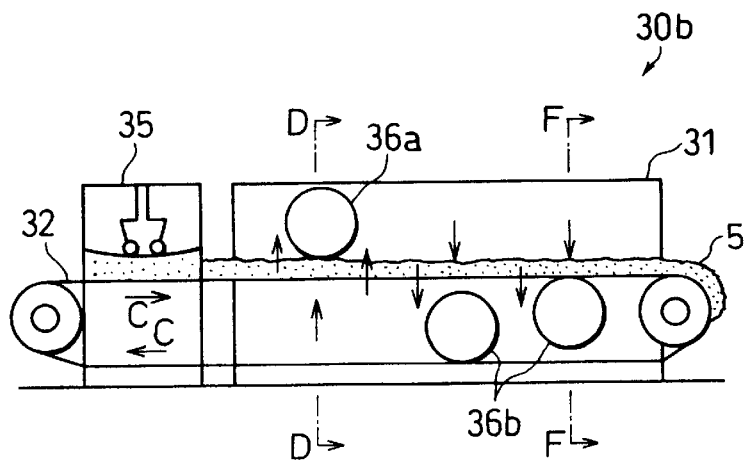
FIG. 4(a) is a cross section showing an arrangement of a through-flow band dryer used in the drying step of the manufacturing method of absorbent resin of the present invention.
Figure 4B:
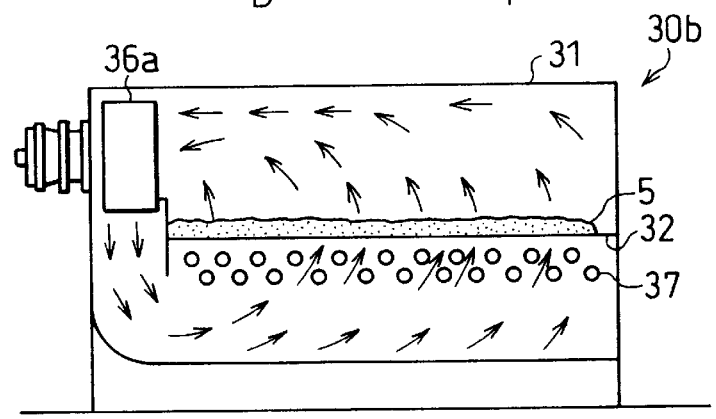
FIG. 4(b) is a cross section of the through-flow band dryer taken on line D—D of FIG. 4(a)

On the other hand, the band dryer using through-flow includes a through-flow band dryer. As shown in FIG. 4(a), a through-flow band dryer 30b is identical with the parallel flow band-tunnel dryer in that it includes the endless band 32 driven in a direction indicated by arrows C by an unillustrated drying device in the tunnel drying chamber 31. However, it is different in that, as shown in FIGS. 4(b) and 4(c), hot air is blown from above and below the hydrogel 5 placed on the band 32.

As shown in FIG. 4(a), the hydrogel 5 is supplied on the band 32 from a hydrogel supplier 35, and it reaches the vicinity of a first fan 36a provided above the band 32 as the band 32 turns. As shown in FIG. 4(b), air heated by an air heater 37 provided below the band 32 is blown from bottom to top (direction indicated by arrows) by the first fan 36a in the vicinity thereof. By flowing air through in this manner, the hydrogel 5 on the side touching the band 32 is mainly dried.

Figure 4C:
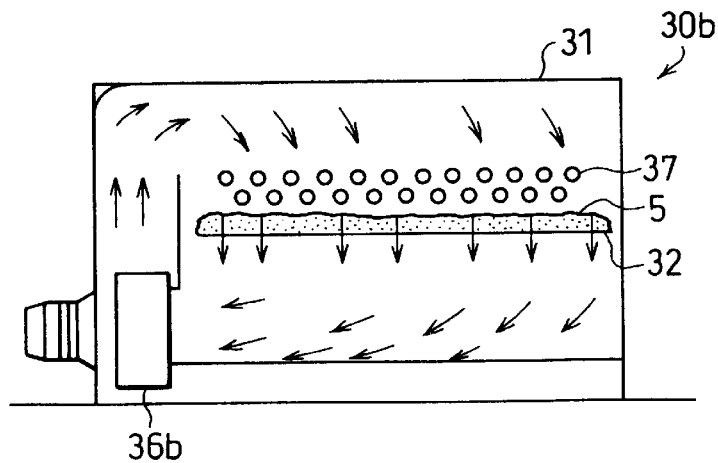
FIG. 4(c) is a cross section of the through-flow band dryer taken on line E—E of FIG. 4(a)

On the other hand, when the hydrogel 5 reaches the vicinity of a second fan 36b provided below the band 32 as the band 32 turns, as shown in FIG. 4(c), air heated by the air heater 37 provided above the band 32 is blown from top to bottom (direction indicted by arrows) by the second fan 36b. By flowing air through in this manner, the hydrogel 5 on the other side (which does not touch the band 32) is mainly dried.

Since each type of the band dryers can dry the hydrogel continuously, compared with the box-type dryer or drum dryer, it can be used more preferably as a dryer when mass-producing the absorbent resin. The band dryer is advantageous in that the hydrogel can be placed continuously without depending on the elasticity or strength of the hydrogel, and that troubles caused when the hydrogel adheres to the dryer occurs less frequently. Thus, the drying method using the band dryer is more preferable than the others in the manufacturing method of the absorbent resin of the present invention.

The dried product of the hydrogel obtained by the drying method using any of the above agglomerating dryers starts to agglomerate and forms aggregates during the drying step, thereby making it impossible to obtain a powdery dried product. For this reason, after the drying step of the above drying method, a step (disintegrating step) of disintegrating the aggregates is conducted to obtain a powdery dried product.

In the present embodiment, the action of roughly crushing the aggregates is referred to as "disintegrating", and a step of conducing the "disintegrating" is referred to as the "disintegrating step". To be more specific, if the aggregates are in the form of plates having a width of 20–200 cm and a thickness of 5–100 mm, the action of crushing the plates of the aggregates to angular aggregates of 20–100 m cube is referred to as the "disintegrating". When disintegrating the plates of the aggregates, a part thereof is loosed and reproduced as primary particles, or a part of the primary particles may be further crushed.

On the other hand, in the present embodiment, the action of pulverizing the angular aggregates obtained by the disintegrating to powdery aggregates and primary particles is referred to as "coarse-pulverizing", and a step of conducting the "coarse-pulverizing" is referred to as the "coarse-pulverizing step". To be more specific, when the angular aggregates obtained by the disintegrating step is 20–100 mm cube, the action of pulverizing the angular aggregates to powdery aggregates of 1–100 mm cube is referred to as "coarse-pulverizing". By the coarse-pulverizing, primary particles are also reproduced, and not only the powdery aggregates, but also a part of the primary particles are pulverized.

Further, in the present embodiment, the action of further pulverizing the angular aggregates obtained by the disintegrating, powdery aggregates or primary particles obtained by the coarse-pulverizing to finer particles, namely the absorbent resin as the final object, is referred to as "pulverizing", and a step of conducting the "pulverizing" is referred to as the "pulverizing step". To be more specific, if the powdery aggregates obtained by the coarse-pulverizing are of 1–10 mm cube, the action of pulverizing the same to particles of 0.01–1 mm cube as the absorbent resin is referred to as "pulverizing".

Methods of crushing the hydrogel in the disintegrating step, coarse-pulverizing step, and pulverizing step are not especially limited. For example, the disintegrating by applying a pressure is preferably used as the disintegrating method. Alternatively, when the band dryer is used as the agglomerating dryer, the following method is available. That is, a kneader which rotates faster than the band is provided at the downstream end of the band, so that the dried aggregates are caused to break up while they are drawn into the kneader.

Also, in the coarse-pulverizing step after the disintegrating step, for example, a method of coarse-pulverizing the aggregates by a pin mill equipped with a plurality of pins protruding at regular intervals and a plurality of pins which engage with the former is available.

On the other hand, any of the aforementioned methods can be used in the pulverizing step, but the method used therein is not especially limited. However, since this pulverizing step is conducted immediately before the step of obtaining the absorbent resin as the final product, the dried product has to be pulverized more finely. Thus, high-speed rotary pulverizers, such as a pin mill, a hammer mill, and a roll mill, a pneumatic pulverizer, a ball mill, a disintegrator which disintegrates the plates of aggregates by sandwiching the same between two teeth plates and compressing the same, a shredder, or a biaxial or triaxial screw type pulverizer can be suitably used as the pulverizer used in the pulverizing step.

When pulverizing a small amount of the dried product, the dried product may be crushed by a hammer. Further, in case that the drum dryer is used, if two rotating drums are provided to oppose each other, the dried product can be coarse-pulverized by letting the same pass through the rotating drums.

Of all the available pulverizers, when the band dryer is used in the drying step, a roll mill having one or more pairs of rolls, more preferably the one having two or more pairs of rolls, and most preferably the one having about three pairs of rolls is used. Regardless of its relatively simple arrangement, the roll mill functions so sophisticatedly that it can pulverize a material subject to pulverization (the dried product of the hydrogel, herein) in a satisfactory manner. The roll mill is particularly preferable when the band dryer is used, because the dried product can be pulverized continuously along with the drying action by the band dryer.

As has been discussed, by using a roll mill having two or more pairs of rolls, a pulverized product having a sharp particle size distribution, which contains less amount of fine powder with a particle size of 100 $\mu$m or less, can be obtained. The roll mill having a roll with vertical or horizontal grooves is preferably used. In case of using a pair of the rolls turning in opposite directions, the two rolls may turn at the same rate or the one may turn faster than the other.

In the manufacturing method of the absorbent resin of the present embodiment, the agglomerating dryer is used in the drying step. For this reason, powdery hydrogel starts to agglomerate along with the drying, and forms plates of aggregates. Thus, the absorbent resin is obtained by disintegrating the aggregates in the disintegrating step, and subsequently, pulverizing the disintegrated aggregates further. Here, if the plates of the aggregates are placed in the dryer as a layer of a uniform thickness during the drying step, the hydrogel can be dried in a very uniform manner, thereby making it possible to obtain high-quality absorbent resin.

However, in practical applications, it is quite difficult to do so in the agglomerating type dryer. In addition, if the hydrogel contains particles larger than 10 mm, the production of a incompletely dried product of the hydrogel can not be prevented by any of the aforementioned methods using the agglomerating type dryers. Once the incompletely dried product is produced, a trouble such that the incompletely dried product adheres to the pulverizer used in the subsequent pulverizing step and stops the pulverizer readily occurs. Hence, the manufacturing efficiency of the absorbent resin is reduced; moreover, the physical properties of the resulting absorbent resin are deteriorated if the incompletely dried product is mixed into the dried product.

In order to solve the above problem, the manufacturing method of the absorbent resin of the present invention includes the separating step of separating the incompletely dried product of the hydrogel mixed in the dried product of the hydrogel from the same. In other words, according to the manufacturing method of absorbent resin of the present invention, the incompletely dried product of the hydrogel is separated from the powdery dried product of the hydrogel obtained in the disintegrating step or coarse-pulverizing step conducted after the drying step. Consequently, high-quality absorbent resin can be manufactured efficiently.

In the separating step, the incompletely dried product is separated from the dried product by classifying the powdery dried product. This action is taken based on the properties of the hydrogel set forth below.

When plates of aggregates obtained in the drying step by the agglomerating dryer are disintegrated, the dried product of the hydrogel in the aggregates are readily disintegrated to powder, but the incompletely dried product of the hydrogel in the aggregates are not readily broken because it is in the form of rubber having good viscosity. Hence, the powdery dried product obtained in the disintegrating step is composed of particles of the dried product having a relatively small volume and the incompletely dried product which was not broken in the disintegrating step and thereby having a large volume.

Thus, the incompletely dried product of large particles are separated from the dried product of small particles by sifting (classifying) the powdery dried product through a sieve with a predetermined opening size. By classifying the powdery dried product based on a particle size through a sieve or the like, the incompletely dried product can be readily and efficiently separated from the dried product without using any complex device.

Here, the water content of the dried product of the hydrogel obtained in the drying step is 15 wt % or less. In other words, in the manufacturing method of the absorbent resin of the present invention, the hydrogel having water content exceeding 15 wt % is deemed as the incompletely dried product.

When the polymerization ends, approximately 30–40 wt % of the hydrogel is solid. In other words, the water content of the hydrogel is approximately 60–70 wt %. If the hydrogel is dried and the solid therein reduces to 50–70 wt %, or the water content increases to 30–50 wt %, the viscosity of the hydrogel increases drastically. Under these conditions, particles of the hydrogel readily agglomerate and form aggregates in the end.

However, if the solid in the hydrogel exceeds 85–90 wt %, or the water content is reduced to approximately 10–15 wt %, the viscosity of the hydrogel drops sharply and it is readily crushed by an external force. In other words, the hydrogel having water content exceeding 15 wt % is rubber gel having very high viscosity, and therefore, can not be pulverized by a pulverizer or the like and adheres to the pulverizer to the extent that the pulverizer is stopped. On the other hand, when the water content is reduced to 15 wt % or less, the viscosity of the hydrogel drops sharply and it can be readily pulverized by a pulverizer.

Thus, by conducting the drying step with the agglomerating dryer, the dried product forms aggregates, but a portion having water content of 15 wt % or less can be readily disintegrated when the aggregates are disintegrated. On the other hand, a portion having water content exceeding 15 wt % is not readily disintegrated, and remains as large aggregates.

By conducting the drying step with the non-agglomerating type dryer, both the dried and incompletely dried products are produced in the form of powdery particles. However, since the particles of the incompletely dried product have higher water content and larger viscosity than those of the dried product, the former agglomerate or the particles of the dried product adhere to the same. Thus, compared with the latter, the former are relatively large and heavy.

According to the manufacturing method of the absorbent resin of the present invention, the incompletely dried product can be readily separated from the dried product by utilizing the above-mentioned properties of the hydrogel. To be more specific, since the incompletely dried product of the hydrogel (with water content exceeding 15 wt %) becomes relatively large compared with the dried product of the hydrogel (with water content of 15 wt % or less), the incompletely dried product can be readily separated from the dried product by sifting (classifying) the powdery dried product obtained after the drying step through a sieve or the like or by classifying the particles of the dried product by a pneumatic dryer based on a particle size or a weight.

In other words, because of the properties of the hydrogel, the incompletely dried product of the hydrogel (with water content exceeding 15 wt %) is not readily disintegrated or pulverized, and for this reason, the incompletely dried product is not broken in the disintegrating step, and remains as large particles in general. That is, particles of the incompletely dried product of the hydrogel remain as large particles not because it is not disintegrated in a satisfactory manner, but because it is not disintegrated. Hence, by classifying the powdery dried product, the incompletely dried product in the form of large particles can be readily separated from the dried product.

In some cases, the dried product adhere to the incompletely dried product having good viscosity or the incompletely dried product which is dried to some extent does not remain as gel but turns to rubber having a high-water-content matter coated with a dry surface. In the present invention, these products are encompassed in the incompletely dried product of the hydrogel.

The water content of the hydrogel is computed in the following manner. That is, a weight of sample hydrogel is measured before it is dried, and a weight of the same is measured again after it is dried for 3 hours at 180° C. Then, the water content is computed in accordance with the following equation based on a change in weight before and after the drying:

$$\text{water content } (\%) = \{(wt_0 - wt_1)/wt_0\} \times 100$$

where $wt_0$ is a weight of the hydrogel before the drying and $wt_1$ is a weight of the hydrogel after the drying.

Figure 5:
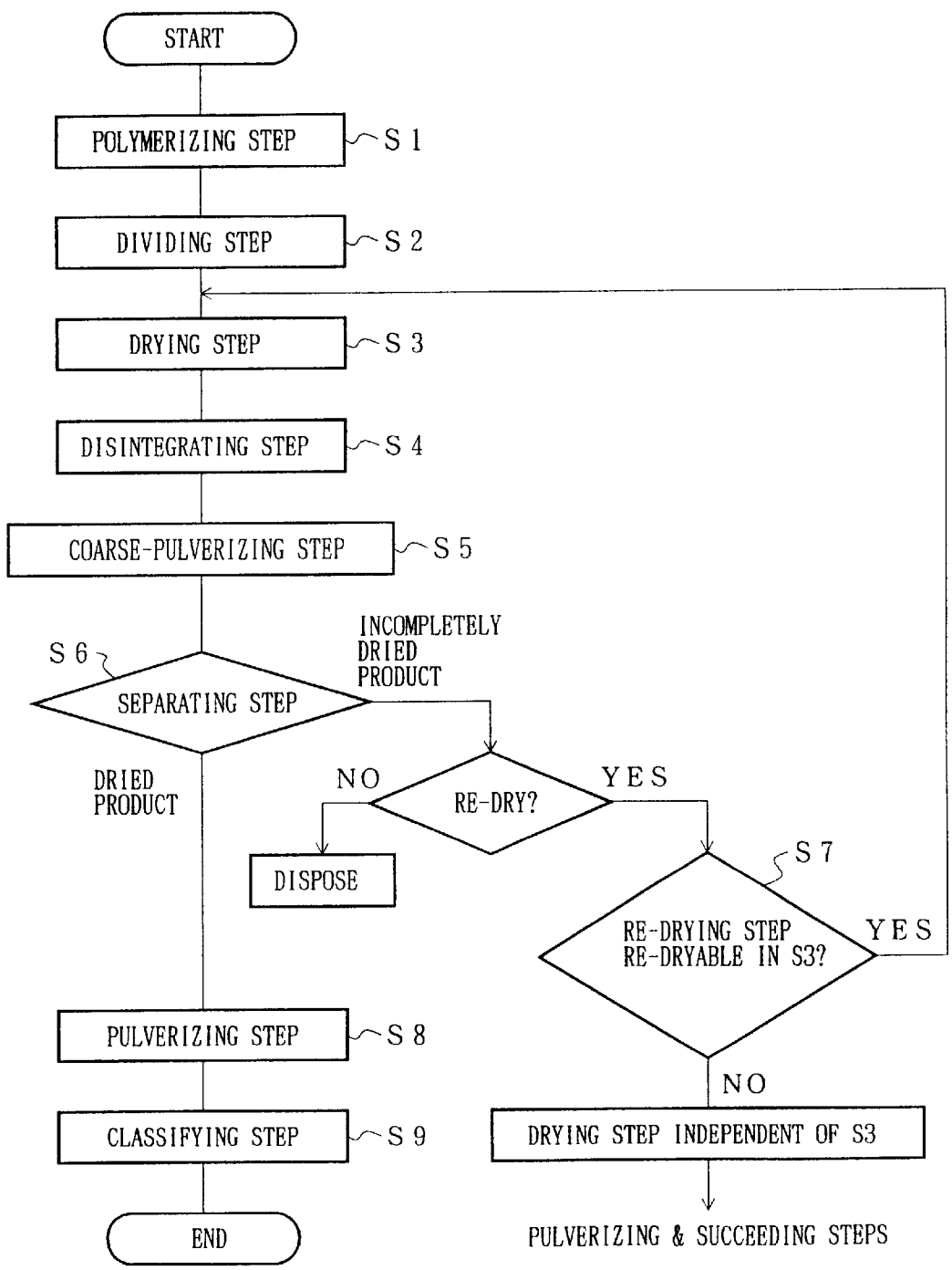
FIG. 5 is a flowchart detailing a manufacturing process of absorbent resin of the present invention when any of the dryers of FIGS. 1 through 4(a) is used.

Next, with reference to FIG. 5, the following will detail the manufacturing process of the absorbent resin including the above-explained disintegrating and separating steps in accordance with the present embodiment.

Initially, in Step 1 (hereinafter, Step is abbreviated to S), hydrogel is obtained by subjecting an ethylenically unsaturated monomer to aqueous solution polymerization in the presence of a slight amount of a crosslinking agent (polymerizing step). In S2, the resulting hydrogel is divided to fine particles (dividing step). In S3, the resulting hydrogel is dried by any of the methods using the above-explained dryers (drying step). Note that the hydrogel is divided to powder in S2 (dividing step), but it forms plates of aggregates in S3 (drying step).

In S4, the plates of aggregates are disintegrated by a disintegrator or the like to angular aggregates of the dried product of the hydrogel (disintegrating step). Here, the coarse-pulverizing step of further breaking up the angular aggregates of the hydrogel obtained in the disintegrating step may be added as S5. It is preferable to add the coarse-pulverizing step when the angular aggregates obtained in the disintegrating step are too large to separate the incompletely dried product from the dried product in a satisfactory manner in the separating step conducted later.

After S4 (disintegrating step) or S5 (coarse-pulverizing step), the incompletely dried product of the hydrogel contained in the angular aggregates or particles of aggregates is separated therefrom in S6 (separating step). As has been discussed above, it is particularly preferable to classify the particles by sifting the same through a sieve or the like in accordance with a particle size. Here, some of the dried product may adhere to the incompletely dried product and separated from the rest of the dried product, but it does not cause any inconvenience unless a substantial portion of the dried product is lost. In short, it does not cause any inconvenience unless the incompletely dried product is delivered to the pulverizing step where the final product is obtained.

The incompletely dried product of the hydrogel separated in S6 (separating step) may be collected from time to time, and dried again until its water content is reduced to a predetermined range (S7, or re-drying step) Before the re-drying step is conducted, whether the incompletely dried product should be dried again or not is decided. If an amount of the incompletely dried product separated and collected in S6 is too small and re-using the same would only increase the cost, the incompletely dried product is disposed. In contrast, when it is decided that the incompletely dried product should be dried again, an optimal drying method is selected based on the condition of the collected incompletely dried product, the cost or manufacturing efficiency in consideration of the entire manufacturing process of the absorbent resin.

For example, in the re-drying step, the incompletely dried product may be fed back to the dryer used in S3 (drying step), or dried again by another dryer. Here, if the incompletely dried product can be dried in a satisfactory manner by the dryer used in S3, it is preferable to feed back the incompletely dried product because not only can the cost be cut, but also the manufacturing process can be simplified.

On the other hand, if the incompletely dried product can not be dried again in a satisfactory manner when fed back to the dryer used in S3, it is efficient to dry the incompletely dried product again by another dryer. Here, a dryer of the same type as the one used in S3 or a different type can be used as "another dryer", and the type of the dryer can be selected adequately in accordance with the condition of the incompletely dried product. Also, angular aggregates or powdery aggregates of the dried product obtained by the re-drying step which is conducted independently of S3 are pulverized adequately, and subsequently classified to a certain particle size.

Then, in S8, the angular aggregates of the dried product from which the incompletely dried product has been separated, particles of aggregates, and primary particles are pulverized to primary particles having a predetermined particle size or smaller (for example, 850 $\mu$m or less) (pulverizing step). Finally, the pulverized product thus obtained is classified in accordance with a particle size within a predetermined range, whereby the absorbent resin is obtained as the final product in S9 (classifying step).

In S8, the dried product from which the incompletely dried product has been separated may be classified before the pulverizing step, so that the job in the pulverizing step is reduced and the production of fine powder having a particle size of 100 $\mu$m or less is prevented. In short, primary particles having a particle size of 850 $\mu$m or less can be eliminated at this point, and added to the final product later in an adequate manner.

The pulverized product having a particle size within a predetermined range obtained by the classifying step is the absorbent resin as the final product. Alternatively, the pulverized product may be further delivered to a granulating step or a surface crosslinking step (not shown in the drawing). On the other hand, an insufficiently pulverized product having a larger particle size than the predetermined range is pulverized again, or disposed when an amount of the same is too small. Consequently, the absorbent resin of the present invention having excellent physical properties can be obtained efficiently.

As has been discussed, according to the manufacturing method of the absorbent resin having the drying step conducted by the agglomerating dryer, the powdery aggregates can be obtained efficiently by adding the disintegrating step, and preferably the coarse-pulverizing step, after the drying step. Further, since the incompletely dried product is separated from the resulting powdery aggregates, the incompletely dried product is not delivered to the pulverizing step, thereby making it possible to prevent the occurrence of troubles in the pulverizing step. Also, since the incompletely dried product is not mixed into the absorbent resin obtained as the final product, high-quality absorbent resin can be obtained efficiently.

Note that S9 (classifying step) is a step generally conducted after the pulverizing step in a conventional manufacturing method of absorbent resin. Thus, the classifying action taken in S9 is totally different from the classifying action taken in S6 (separating step), which is unique to the manufacturing method of the absorbent resin of the present invention.

To be more specific, the classifying step is a step where an insufficiently pulverized product is merely sorted, while the separating step of the present invention is a step where the incompletely dried product of the hydrogel is separated from the dried product of the hydrogel. Thus, if a classifying technique is used in the separating step, the incompletely dried product can be readily separated, but a technique adopted in the separating step is not limited to the classifying technique as long as the incompletely dried product can be separated from the dried-product efficiently.

In addition, in most of the cases, the classifying step is conducted immediately before the step of obtaining the absorbent resin as the final product. For this reason, unlike the separating step of the present invention, it is not a step conducted before the pulverizing step. From these differences, it is apparent that the classifying step and separating step are totally different.

Figure 6:
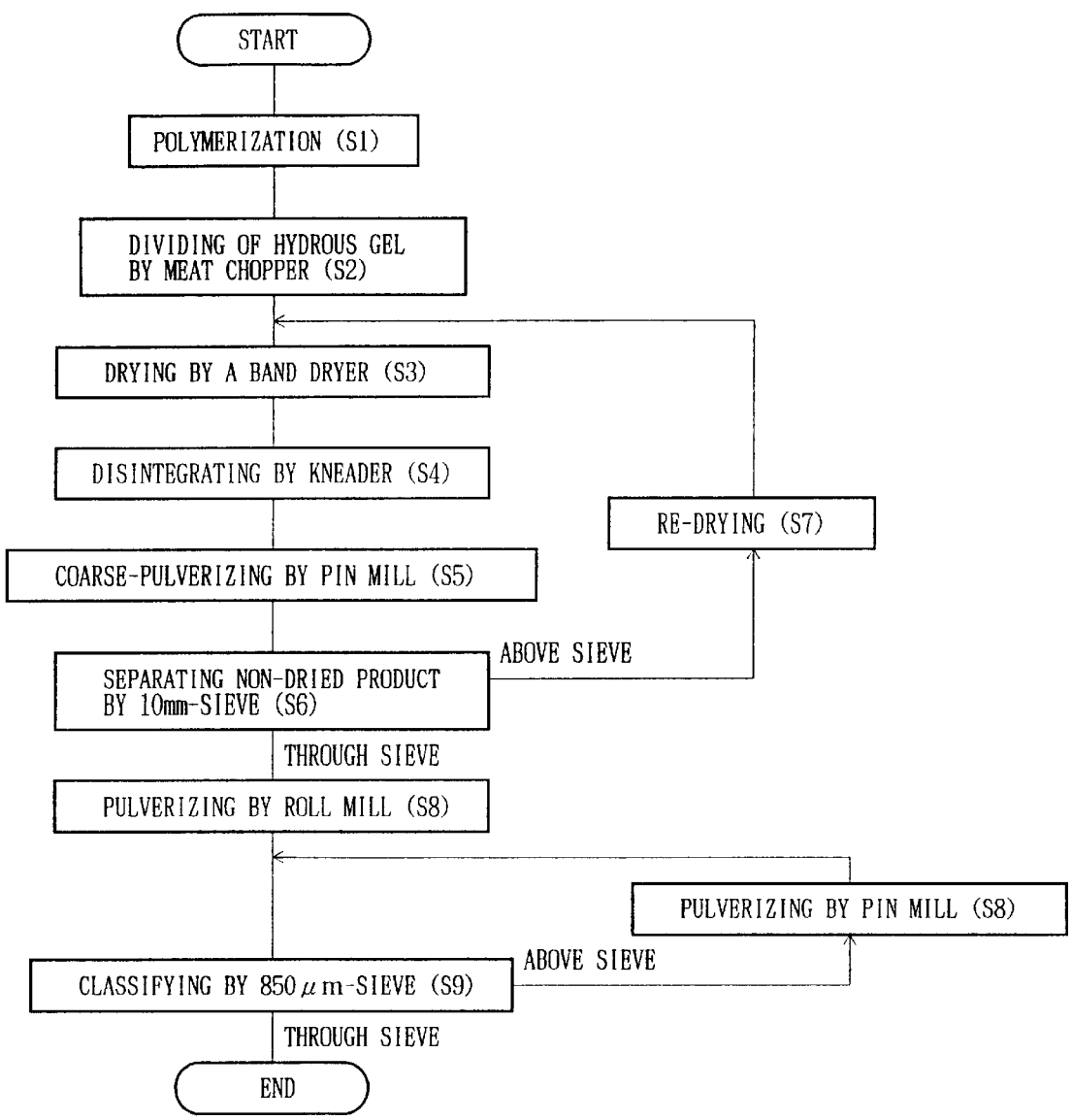

The following will explain in detail the separating step with reference to FIG. 6, so that the difference from the classifying step will be more readily understood. The following will discuss the manufacturing process of the absorbent resin in an example case where the drying step is conducted by the band dryer.

As shown in FIG. 6, after the hydrogel is obtained in S1 explained with reference to FIG. 5, the hydrogel is divided by a meat chopper in S2. Then, the fine particles of the hydrogel are dried by the band dryer in S3. The hydrogel is placed on the band and dried while it is conveyed toward the downstream of the band as the band turns, and eventually starts to agglomerate. A kneader with a number of revolution greater than a moving rate of the band (for example, by a factor of 1.01–10) is provided at the end of the downstream, so that the resulting plates of aggregates are drawn into the kneader and disintegrated (S4).

The angular aggregates obtained by disintegrating the plates of aggregates with the kneader are coarse-pulverizing by a pin mill, whereby particles of aggregates are obtained (S5). The particles of the aggregates, that is, the powdery dried product, include particles of the incompletely dried product. Compared with the particles of the dried product, the particles of the incompletely dried product is relatively large. Thus, the particles of the dried product is sifted (classified) through a sieve (S6).

It is assumed that, after the disintegrating step and coarse-pulverizing step, three kinds of products are obtained: (1) particles or aggregates of the incompletely dried product which were not loosened in the disintegrating and coarse-pulverizing steps; (2) aggregates of the dried product which were loosed in the disintegrating and coarse-pulverizing steps but disintegrated insufficiently to be primary particles; and (3) particles of the dried product which were loosened or coarse-pulverized in a satisfactory manner in the disintegrating and coarse-pulverizing steps.

In terms of the particle sizes, the particles or aggregates of the incompletely dried product set forth in (1) are placed in the first, followed by the aggregates set forth in (2), and the particles set forth in (3). Hence, a sieve with a larger opening size is used in the separating step. The opening size of the sieve used in the separating step can be set adequately depending on the size or amount of the incompletely dried product, but a preferable range is between 5–50 mm and a more preferable range is between 7–20 mm. If the opening is smaller than 5 mm, an amount of the separated incompletely dried product may be increased too much. On the other hand, if the opening is larger than 50 mm, the incompletely dried product may not be separated in a satisfactory manner. For example, in the present embodiment, a sieve with an opening of 10 mm is used to separate the incompletely dried product from the dried product. Hereinafter, a sieve with an opening of 10 mm is referred to as 10 mm-sieve.

After the sifting in the separating step, the product remaining on the 10 mm-sieve, that is, the incompletely dried product having the largest particle size in the powdery dried product (particles and aggregates set forth in (1)) are fed back to the band dryer and dried again (S7). If an amount of the incompletely dried product is too small, it may be disposed. On the other hand, if the incompletely dried product can not be dried again by the band dryer in a satisfactory manner, another dryer may be used.

The product passing through the 10 mm-sieve does not include the incompletely dried product, but includes the coarse-pulverized or crashed aggregates having a relatively large particle size (aggregates set forth in (2)) and primary particles. So, the passing-product is pulverized by a roll mill or the like (S8, pulverizing step). In the process of FIG. 5, S8 (pulverizing step) is conducted after the separating step, and a roll mill having two or more pairs of rolls, a pin mill, a hammer, etc. can be used therein.

Then, in the final step, that is, S9 (classifying step), the pulverized product obtained in the pulverizing step is sifted through a sieve having an opening of 0.85 mm, for example. Since the product which remains on the 0.85 mm-sieve is equivalent to the aggregates set forth in (2), it is pulverized again by the pin mill and sifted through the 0.85 mm-sieve again.

As has been discussed, the classifying action in S6 (separating step) is taken to separate the incompletely dried product (particles and aggregates set forth in (1)) from the dried product. On the other hand, S9 (classifying step) is conducted to separate the aggregates (aggregates set forth in (2)) and primary particles. Thus, S6 (separating step) and S9 (classifying step) are basically different. However, it should be noted that, by adopting the classification based on a particle size in the separating step, the incompletely dried product can be separated from the dried product effectively.

The above-described classifying method using a sieve can be used suitably as the separating method in the separating step. However, other methods are also applicable. For example, a classifying method, by which particles are classified and collected by blowing up small and light particles with hot air, can be adopted. In short, the separating method is not especially limited as long as the incompletely dried product can be separated from the dried product efficiently.

As has been discussed, the manufacturing method of the absorbent resin of the present invention is a method of separating and eliminating the incompletely dried product before the pulverizing step when the hydrogel is dried and pulverized (when the absorbent resin is manufactured as the final product), so that the incompletely dried product of the hydrogel is not mixed into the dried product when pulverizing the dried product in the pulverizing step.

Also, according to the manufacturing method of the absorbent resin of the present invention, the incompletely dried product is separated and eliminated from the powdery dried product by means of sieving using a sieve or the like, because the particles of the incompletely dried product are relatively large compared with those of the dried product.

By adopting the above method, it has become possible to effectively prevent rubber of the incompletely dried hydrogel from adhering to the pulverizer, thereby stopping the smooth pulverizing action, or the operation of the pulverizer, and this effect is particularly obvious when the roll mill is used as the pulverizer. Further, since the incompletely dried product is not mixed into the absorbent resin obtained as the final product, the deterioration of the physical properties of the absorbent resin can be suppressed, thereby making it possible to manufacture the absorbent resin of a higher quality.

Further, the band dryer is most preferably used as the dryer for the hydrogel used in the drying step. Since the band dryer can handle a large volume of the hydrogel continuously, there can be attained an effect that the manufacturing efficiency of the absorbent resin is improved while the manufacturing costs are saved.

In addition, by collecting the incompletely dried product of the hydrogel separated from the dried product of the hydrogel and drying the same again, the manufacturing costs of the absorbent resin can be saved further. Also, if a roll mill having two or more stages is used in the pulverizing step where the dried product of the hydrogel is pulverized to finer particles, namely the absorbent resin as the final product, the pulverized product with a less amount of fine powder can be obtained by a simple arrangement.

Embodiment 2

Referring to FIGS. 7 through 15, the following description will describe another example embodiment of the present invention for purposes of explanation only, without any intention as a definition of the limits of the invention.

Embodiment 1 above described a case where the agglomerating dryer is used in the drying step, and the present embodiment will describe a case where the non-agglomerating type dryer is used in the drying step.

The non-agglomerating type dryer is a dryer which dries the hydrogel with stirring, and since the hydrogel is kept stirred, it does not agglomerate. Examples of the non-agglomerating type dryer include a fluidized-bed dryer, a stirring dryer, a disc dryer, a rotary dryer, a pneumatic dryer, etc.

The following will explain the arrangement of each type of dryer and a manufacturing process of the absorbent resin of the present invention by using each type of dryer. The arrangements of the fluidized-bed dryer, stirring dryer, disc dryer, and rotary dryer, and the manufacturing process of the absorbent resin by using the non-agglomerating type dryer will be explained.

The fluidized-bed dryer dries a material subject to drying (hydrogel) by placing powdery hydrogel on a gas dispersing plate (straightening vane) made of a porous plate or the like, and forming a fluidized layer (fluidized-bed) by sending hot air from below. The fluidized-bed dryer has excellent contacting efficiency between the material subject to drying and hot air, and therefore, is advantageous in that heat is conducted promptly and that the handling capacity is large.

Figure 7:
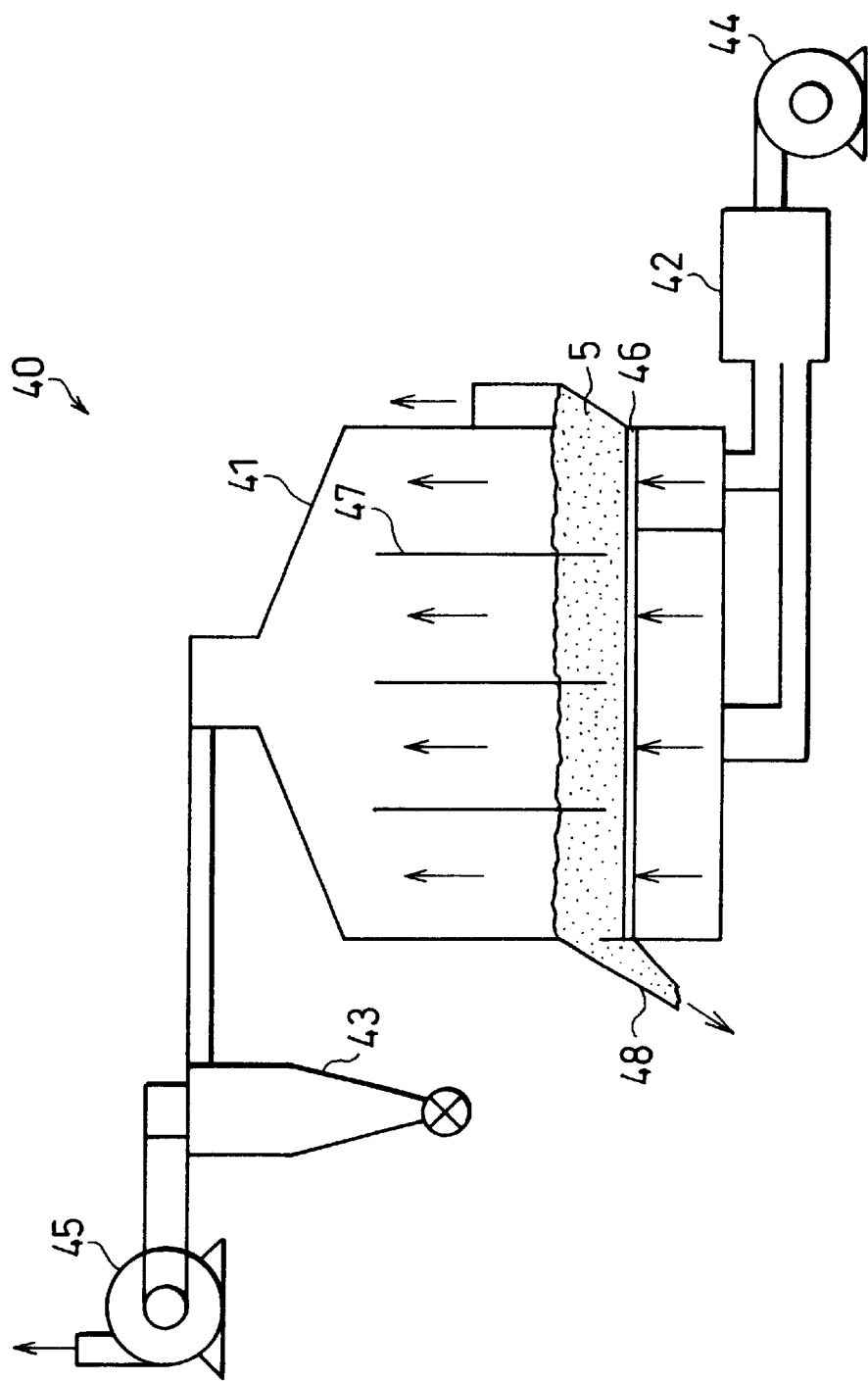
FIG. 7 is a view schematically showing a fluidized-bed dryer used in a drying step of a manufacturing method of absorbent resin in accordance with another embodiment of the present invention.

The fluidized-bed dryer includes a batch type and a continuous type, and the fluidized layer is formed in more than one layer or more than one chamber. For example, as shown in FIG. 7, a fluidized-bed dryer 40 of a longitudinal multi-chamber type includes a drying chamber 41, an air heater 42, a cyclone 43, a fan 4, a blower 45, a dried product outlet 48, etc. Further, the drying chamber 41 is furnished with a plurality of porous plates (straightening vanes) 46 and partitions 47.

In the fluidized-bed dryer 40 of FIG. 7, air sent by the fan 44 is heated by the air heater 42, and starts to flow in the drying chamber 41 upward (direction indicated by arrows). The porous plates 46 are provided beneath the drying chamber 41, and the hydrogel 5 is placed on the top thereof. The hot air is sent to the hydrogel 5 from below, and accordingly, the hydrogel 5 forms a fluidized layer in the drying chamber 41, whereby the hydrogel 5 is dried continuously. Since the interior of the fluidized-bed dryer 40 is divided into a plurality of chambers with the partitions 47 aligned on the porous plate 46 with a space inbetween, a residual time distribution of the hydrogel 5 can be narrowed. Consequently the fluidized-bed dryer 40 can dry the hydrogel 5 efficiently.

The stirring dryer dries a material subject to drying (hydrogel) continuously with stirring by driving the rotor in the drying chamber. The material subject to drying is dried by means of heat conduction or hot air. The material subject to drying may be stirred by stirring blades, but in case of the hydrogel which readily agglomerates like the one used in the manufacturing method of the absorbent resin of the present invention, it is preferable to stir the same by a rotor.

For example, as shown in FIG. 8(a), a stirring dryer 50 equipped with a rotor includes a drum jacket section 51 as a drying chamber, a hot air inlet 52, a hot air outlet 53, an inlet 54 of the material subject to drying, a dried product outlet 55, etc. As shown in FIG. 8(b), a rotor 56 is provided in the drum jacket section 51.

Hot air sent from the hot air inlet 52 passes through the drum jacket section 51, and goes out from the hot air outlet 53. The hydrogel placed in from the inlet 54 is dried with stirring in the drum jacket section 51 while the rotor 56 rotates in a direction indicated by arrows in FIG. 8(b). The dried hydrogel is released from the dried product outlet 55. In this manner, the hydrogel is dried continuously.

The disc dryer is composed of two kinds of discs (large and small) layered in 5–20 stages, and each stage is provided with 2–4 arms extended from the central axis to which stirring blades are attached. For example, as shown in FIG. 9(a), a disc dryer 60 includes a drying chamber 61 having a plurality of discs 62 in multi-stage, a central axis 64 furnished with stirring blades 63, a supplier 65 which supplies a material subject to drying, erofin heaters 66, a bag filter 67, a cyclone 68, a fan 69, etc.

Figure 9B:
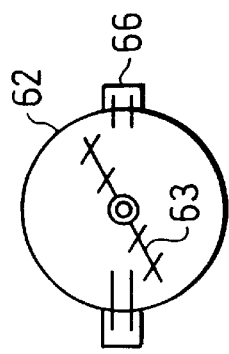
FIG. 9(b) is a view schematically showing an arrangement of a disc and stirring blades of the disc dryer of FIG. 9(a)
Figure 9A:
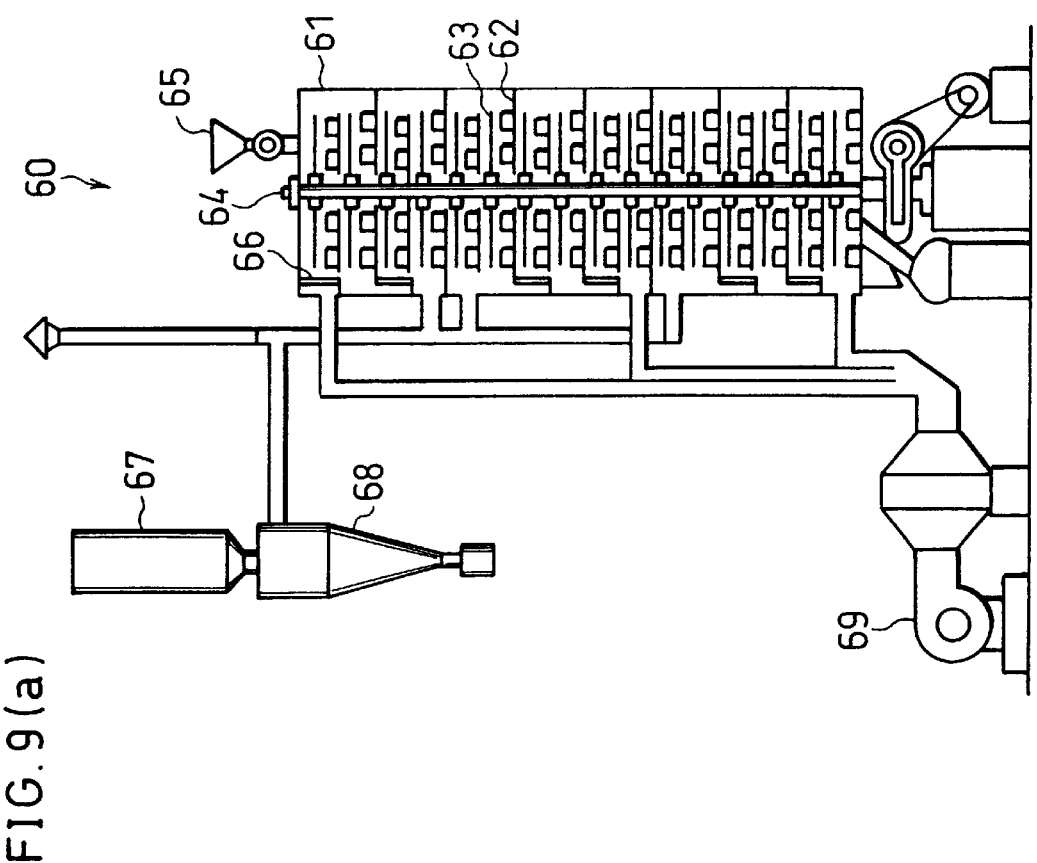
FIG. 9(a) is a view schematically showing an arrangement of a disc dryer used in the drying step of the manufacturing method of absorbent resin of the present invention.
Figure 11:
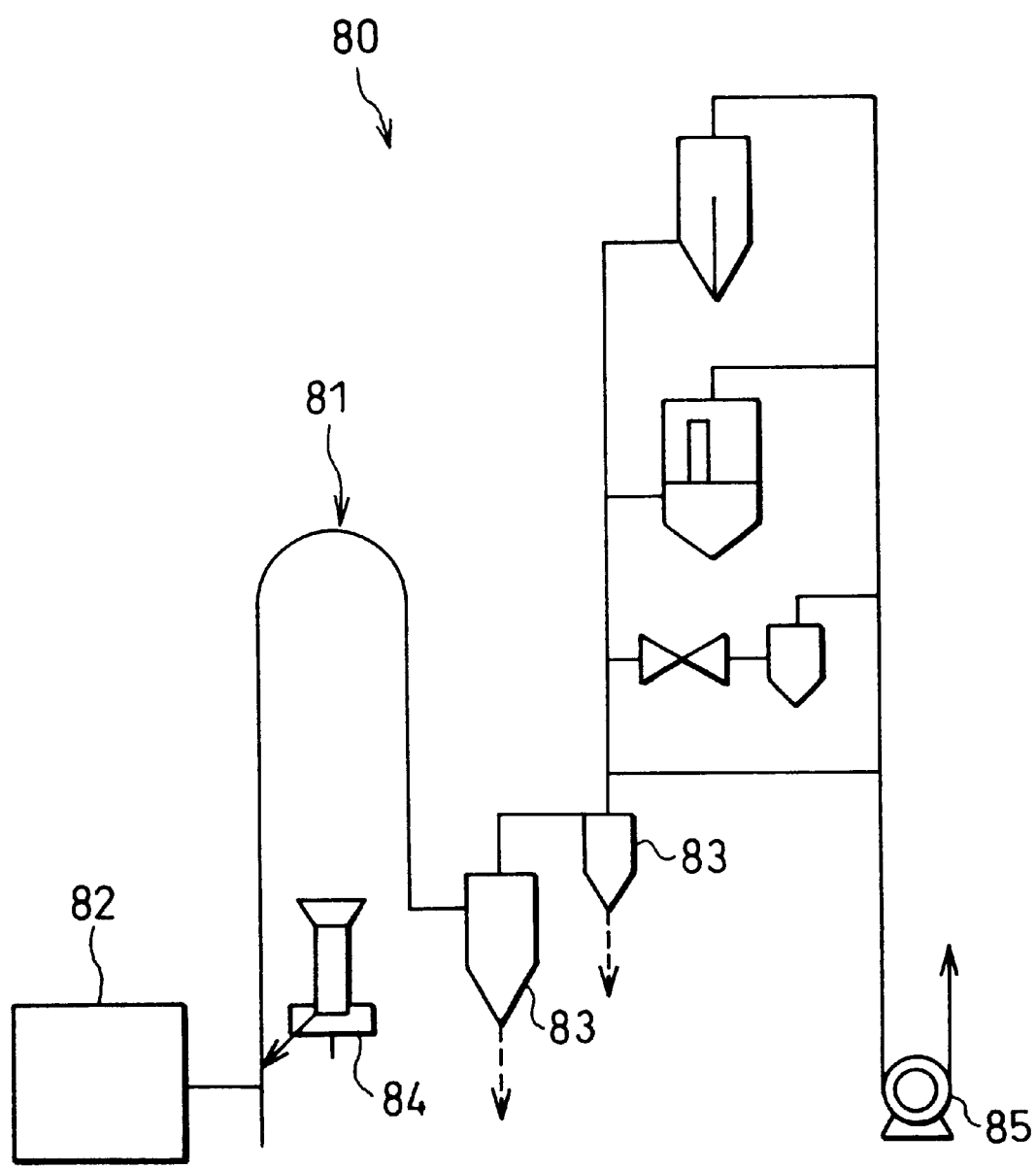
FIG. 11 is a view schematically showing an arrangement of a pneumatic dryer used in the drying step of the manufacturing method of absorbent resin of the present invention.

As shown in FIG. 9(b), the stirring blades 63 are provided to each stage formed by the disc 62 in the manner explained above, and by turning at a rate of 1 rpm–4 rpm, they form mountains or valleys of the material subject to drying (hydrogel) on the disc 62. The material subject to drying is conveyed to the lower stages while forming mountains or valleys which face alternately outward and inward per stage in accordance with the degrees of the stirring blades 63. Consequently, the dried product is taken out at the bottom stage of the disc dryer 60.

The disc dryer 60 dries the material subject to drying with hot air produced by heating air flow from the fan 69 by the erofin heaters 66. However, the drying method is not limited to the foregoing, and the discs may be heated by means of a heating medium. The disc dryer is advantageous in that a drying time can be readily controlled and that it occupies less space.

The rotary dryer is cylindrical, and has a drying chamber provided with scraping-up blades inside. The rotary dryer coveys a material subject to drying (hydrogel) by means of rotation of the drying chamber, so that the material subject to drying is dried while it drops in curtain along with the rotation and brought into contact with hot air blown in parallel or counter.

For example, as shown in FIG. 10(a), a rotary dryer 70 includes a cylindrical drying chamber 71, a driving roller 72 for rotating the drying chamber 71, two supporting rollers 73 which support the drying chamber 71, a hot air inlet 74, a hot air outlet 75, an inlet 76 of the material subject to drying, a dried product outlet 77, etc. As shown in FIG. 10(b), the interior of the drying chamber 71 is provided with a plurality of scraping-up blades 71a aligned inward along a rotating direction of the drying chamber 71 (direction indicated by an arrow).

The drying chamber 71 is driven to rotate by the driving roller 72 while being supported by the supporting rollers 73. Hot air supplied through the hot air inlet 74 flows throughout the drying chamber 71 and comes out through the hot air outlet 75. The hydrogel 5 is placed in the drying chamber 71 through the inlet 76. As shown in FIG. 10(b), the hydrogel 5 placed in this manner is scraped up by the plurality of scraping-up blades 71a and drops in curtain in the drying chamber 71, thereby being repetitively brought into contact with hot air. By this stirring action, the hydrogel 5 is dried and released through the dried product outlet 77.

The rotary dryer is advantageous in that it is structured simply and solidly, and that it can be manipulated easily and readily manufacture the dried product of a large size. Moreover, it can attain high throughput and is very safe. Besides the above-explained type, the rotary dryer includes other types, such as a rotary dryer equipped with a vapor heating pipe and a through-flow rotary dryer.

The pneumatic dryer disperses particles of a material subject to drying in hot air flow, which remains in the form of mud, aggregates, or powder when it is wet and turns into powder when it is dried, and dries the particles by conveying the same afloat in hot air. An example pneumatic dryer 80 shown in FIG. 11 includes a drying chamber 81, a hot air generator 82, a cyclones 83, a supplier 84 of a material subject to drying, a fan 85, etc.

In the drying chamber 81 of the pneumatic dryer 80, hot air is generated by the hot air generator 82 and blown upward by the fan 85. The drying chamber 81 is supplied with the hydrogel from the supplier 84. The supplied hydrogel is blown upward by hot air in the drying chamber 81, whereby the hydrogel is dried promptly and continuously.

If the material subject to drying is in the form of powder, it can be directly placed in the pneumatic dryer. However, if the material subject to drying readily agglomerates and forms aggregates, a disperser may be additionally used to disperse the material subject to drying. Also, a disintegrator may be used when the material subject to drying is coarse-pulverized, or when the material subject to drying is in the form of mud.

In the manufacturing method of the absorbent resin of the present invention, the material subject to drying is in the form of particles of hydrogel, and the hydrogel readily agglomerates and form aggregates. For this reason, the pneumatic dryer may additionally include the disperser, but, as will be described later, it is preferable to prevent the agglomeration by adding a surfactant to the hydrogel to subject the same to surface treatment.

In the pneumatic dryer, the hydrogel is dried until its water content is reduced to a predetermined level by blowing hot air, and the dried hydrogel is dispersed/conveyed. Here, the separating step can be conducted simultaneously with this dispersing/conveying step. To be more specific, since the dried hydrogel (dried product) loses its volume and becomes lighter than the incompletely dried product having high water content as water is removed therefrom, it can be readily dispersed to the upper portion of the drying chamber by hot air flow. On the other hand, since the incompletely dried product has a larger volume and becomes heavier than the dried product because of its high water content, it can not be readily dispersed to the upper portion of the drying chamber. Hence, by providing a classifying section, where the dried product of the hydrogel is separated from the incompletely dried product of the hydrogel, at the upper portion of the drying chamber, the drying step and separating step can be conducted in a single phase.

Further, smaller particles of the dried product are more readily dispersed to the upper portion of the drying chamber by hot air flow. Conversely, larger particles of the dried product are readily collected at the lower portion of the drying chamber. Thus, by providing a pulverizing section at the lower portion of the drying chamber, the larger particles of the dried product can be pulverized, thereby making it possible to conduct the drying step and pulverizing step in a single phase.

In other words, by using the pneumatic dryer in the drying step, the drying step, separating step, and pulverizing step can be conducted in a single phase. Consequently, not only can the manufacturing efficiency of the absorbent resin be improved significantly, but also the manufacturing costs can be saved.

Figure 12:
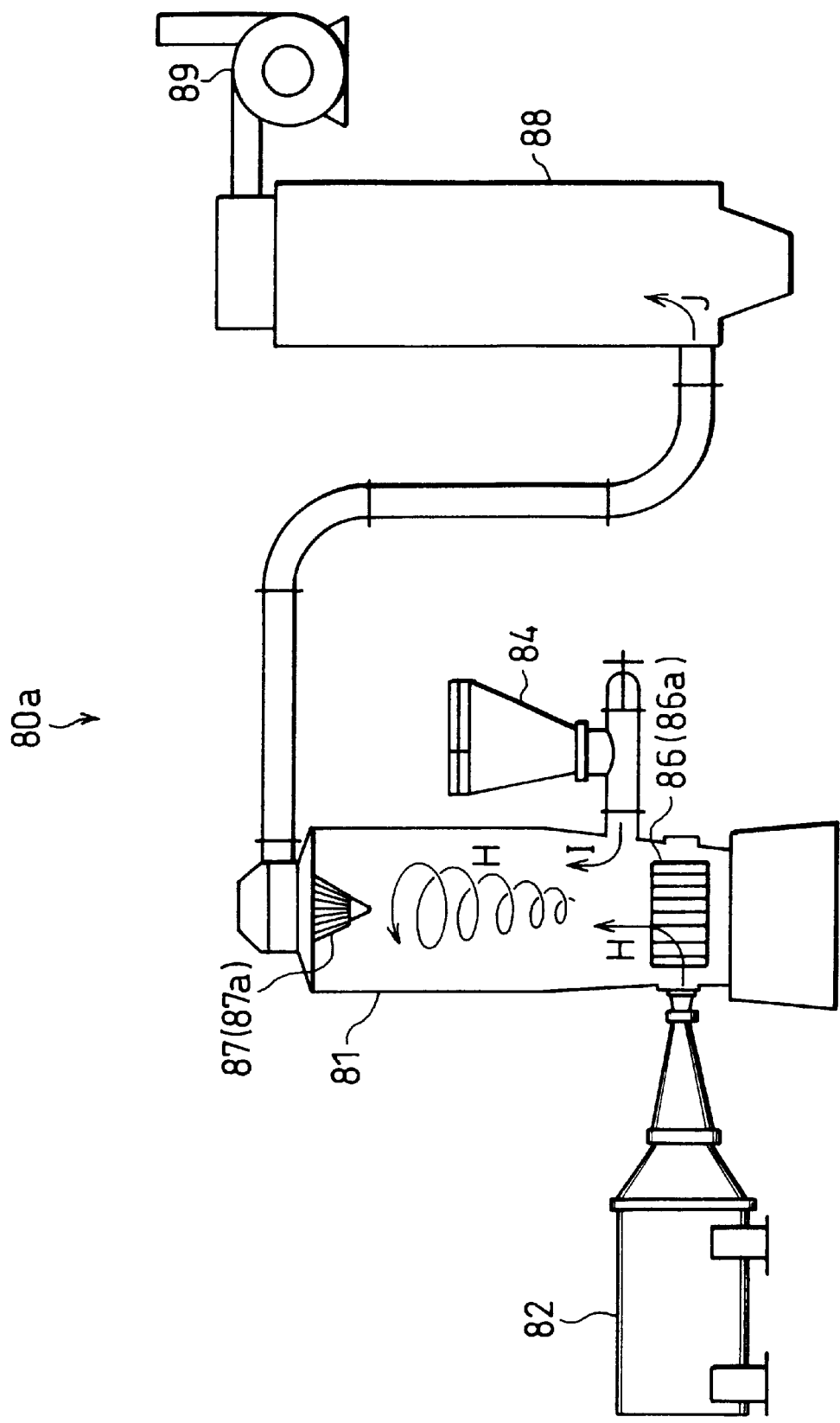
FIG. 12 is a view schematically showing a pneumatic dryer used in the drying step of the manufacturing method of absorbent resin of the present invention, which is equipped with a pulverizing section and a classifying section.

FIG. 12 shows a pneumatic dryer 80a as an example of the pneumatic dryer capable of conducting the three steps—drying, separating, and pulverizing steps—in a single phase, and it includes a drying chamber 81, a hot-air generator 82, a supplier 84 of a material subject to drying, a pulverizing section (pulverizer) 86, a classifying section (classifier) 87, a dried product collecting section 88, a blower 89, etc.

Figure 13A:
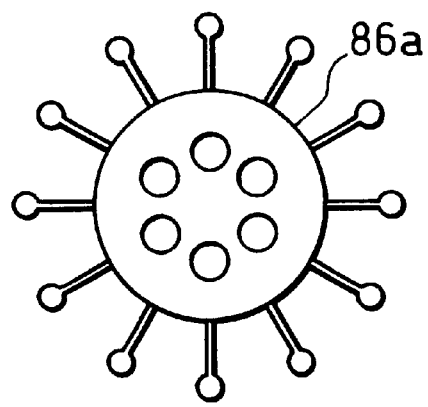
FIG. 13(a) is a view depicting an arrangement of the pulverizing section of the pneumatic dryer of FIG. 12.
Figure 13B:
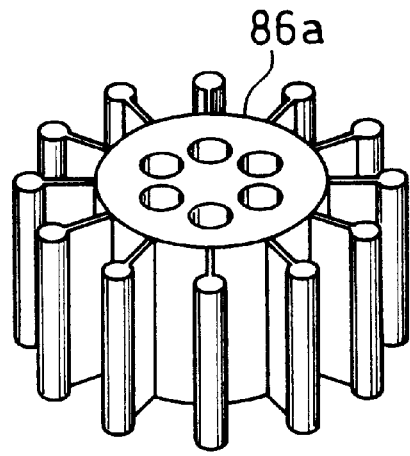
FIG. 13(b) is a view depicting another arrangement of the pulverizing section of the pneumatic dryer of FIG. 12.
Figure 14A:
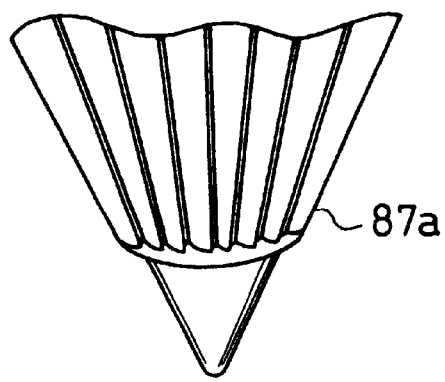
FIG. 14(a) is a view depicting an arrangement of the classifying section of the pneumatic dryer of FIG. 12.
Figure 14B:
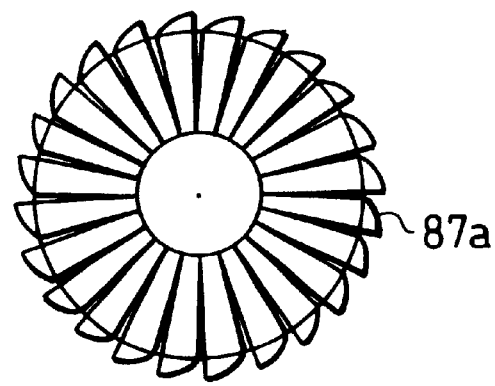
FIG. 14(b) is a view depicting another arrangement of the classifying section of the pneumatic dryer of FIG. 12.

For example, the drying chamber 81 is cylindrical, and the pulverizing section 86 is provided at the lower portion of the drying chamber 81 while the classifying section 87 is provided at the upper portion of the drying chamber 81 in such a manner as to oppose the pulverizing section 86. For example, available as the pulverizing section 86 is a stirrup-type pulverizer 86a having a plurality of pulverizing blades which protrude from the cylindrical main body toward the outer circumference as shown in FIGS. 13(a) and 13(b). Also, available as the classifying section 87 is a conical classifier 87a, whose vertex points out to the lower portion of the drying chamber 81 (that is, the pulverizing section 86 side) and whose surface is provided with classifying blades as shown in FIGS. 14(a) and 14(b).

The pneumatic dryer 80a is identical with the pneumatic dryer 80 in that, in the drying chamber 81, hot air is generated and blown upward (direction indicated by arrows H in the drawing) and the hydrogel supplied from the supplier 84 (in the direction indicated by an arrow I) is blown up in spiral by hot air. However, the former is different from the latter in the following points. That is, since the stirrup-type pulverizer 86a is provided at the lower portion of the drying chamber 81, large particles of the hydrogel are pulverized by the stirrup-type pulverizer 86a, and the pulverized hydrogel is more readily blown up and dried by hot air.

The particles of the hydrogel dried and blown up in the above manner are classified by the classifier 87a, and if they are of a predetermined particle size, they are directly sent to the dried product collecting section 88 (in the direction indicated by an arrow J). The particles of the hydrogel larger than the predetermined particle size are pulverized again by the stirrup-type pulverizer 86a until they are pulverized to particles of the predetermined particle size, after which they are collected to the dried product collecting section 88 through the classifier 87a.

As has been discussed, the classifier 87a of the pneumatic dryer 80a does not merely separate the incompletely dried product from the dried product, but isolates the dried product pulverized to particles of the predetermined particle size by the stirrup-type pulverizer 86a alone. Thus, the pneumatic dryer 80a repeats the drying process until the whole incompletely dried product is dried, but it never happens that the hydrogel is dried exceedingly and remains in the pneumatic dryer. Therefore, unlike the other dryers explained above, it is not necessary to feed back the incompletely dried product or dry the incompletely dried product by another dryer again.

In other words, the pneumatic dryer 80a is advantageous in that not only can the manufacturing process be shortened markedly, but also the drying time can be relatively short. The pneumatic dryer 80a is advantageous further in that it attains high heat efficiency and high throughput regardless of its simple structure and compact size. For the above reasons, the drying method using the pneumatic dryer 80a is particularly preferable in the manufacturing method of the absorbent resin of the present invention.

Figure 15:
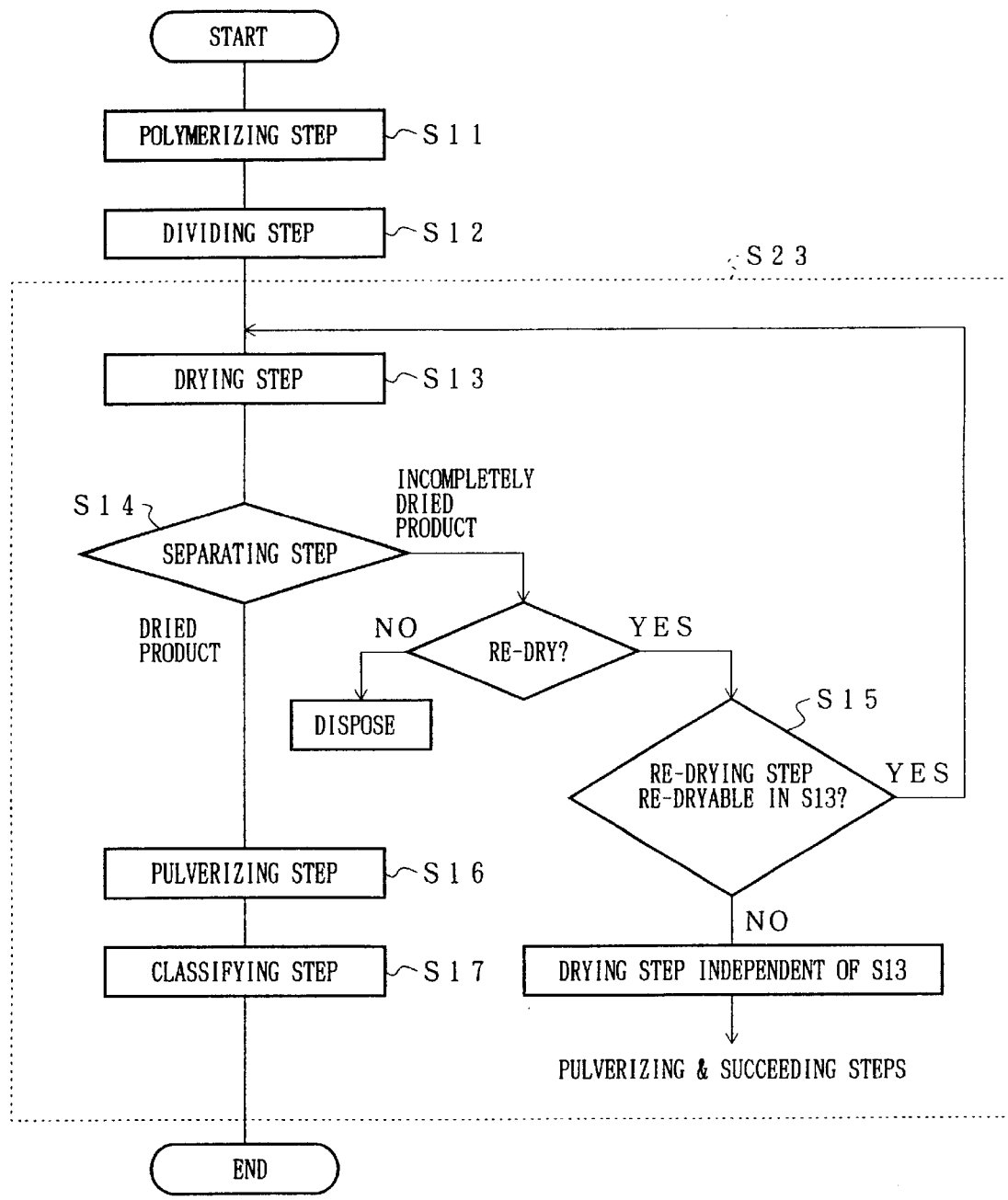
FIG. 15 is a flowchart detailing a manufacturing process of absorbent resin of the present invention when any of the dryers of FIGS. 7 through 12 is used.

Next, with reference to FIG. 15, the following will explain the manufacturing process of the absorbent resin using the above-explained non-agglomerating type dryer in accordance with the present embodiment. The manufacturing process of the absorbent resin is preferably composed of 7 steps (hereinafter, Step is abbreviated to S).

In the first place, S11 is the same as S1 of the manufacturing process using the agglomerating dryer (Embodiment 1). Then, in S12, the resulting hydrogel is divided (dividing step), but this refining step can be omitted. A surfactant is added to the fine particles of the hydrogel so as to prevent agglomeration. The surfactant can be added in any of the steps conducted before or while the hydrogel is dried. However, it is preferable to add the surfactant to the powdery hydrogel before the refining step or during the coarse-pulverizing step, because in this case, the agglomeration of the hydrogel during the drying step can be avoided more effectively. Next, in S13, the hydrogel is dried by the above-explained non-agglomerating type dryer (drying step).

The powdery product obtained in the drying step (S13) is a mixture of the particles of the dried product and particles of the incompletely dried product. Assume that the particles of the dried product and those of the incompletely dried product are made of a crosslinked polymer in the same weight, then the particles of the incompletely dried product have larger volume and become heavier than those of the dried product because of its high water content. Also, since the particles of the incompletely dried product have good viscosity, they readily agglomerate or the particles of the dried product adhere to the same, thereby having a larger volume than those of the dried product.

In the powdery dried product obtained by the drying step, the particles of the incompletely dried product are relatively large compared with those of the dried product. Thus, in S14, the powdery dried product is classified to particles having a particle size within a predetermined range by sifting the same through a sieve or the like (separating step) in the same manner as Embodiment 1. By this classification, the incompletely dried product can be separated from the dried product efficiently.

The separated incompletely dried product is delivered to S15 (re-drying step) or disposed in an adequate manner. In the re-drying step, as was in Embodiment 1, it is decided whether the incompletely dried product is fed back to S13 or dried again by another dryer, whichever is the more convenient. Succeeding S16 and S17 are identical with S8 and S9 in Embodiment 1, respectively, and the explanation thereof is not repeated herein. In this manner, the absorbent resin of the present invention having excellent physical properties can be obtained efficiently.

As has been discussed above, when the non-agglomerating type dryer is used in the drying step of the present embodiment, the hydrogel does not agglomerate along the drying. Thus, unlike the case where the hydrogel agglomerates, the disintegrating step can be omitted.

Herein, S12 (dividing step), S14 (separating step), and S17 (classifying step) can adopt the same methods explained in Embodiment 1, and the explanation thereof is omitted.

In the manufacturing method of the absorbent resin of the present invention, it is particularly preferable to use the pneumatic dryer 80a of FIG. 12 which can conduct the drying, pulverizing, and separating steps in a single phase. In this case, steps denoted as S13 through S17 in the manufacturing process of FIG. 15 (enclosed in a dotted line and referred to collectively as S23) can be conducted in a single phase.

In other words, in the manufacturing method of the absorbent resin of the present invention, as was explained in Embodiment 1, the incompletely dried product is separated from the dried product by classification in the separating step. Since the pneumatic dryer 80a conducts the separating step and pulverizing step simultaneously, the classifying step and separating step can be conducted in a single phase. Consequently, the absorbent resin can be manufactured in substantially two phases.

In case of the drying step using the non-agglomerating type dryer, that is, in case that the powdery hydrogel is dried with stirring, if the hydrogel agglomerates during the drying step, drying is not conducted smoothly, and in some cases, drying may not be conducted. To prevent such an inconvenience, a surfactant used as a lubricant is added to the hydrogel before or during the drying. By adding the surfactant, the powdery hydrogel is surface-treated, and agglomeration of the same can be effectively suppressed.

Available as the surfactant are various kinds of surfactants including an anionic surfactant, a non-ionic surfactant, a cationic surfactant, an ampholytic surfactant, etc.

Examples of the anionic surfactant include:

salts of fatty acids, such as soap of mixed fatty acid sodium, soap of semi-solid beef tallow fatty acid sodium, soap of sodium stearate, soap of potassium oleate, and soap of caster oil potassium;

salts of alkyl sulfuric ester, such as sodium lauryl sulfate, higher alcohol of sodium sulfate, and triethanolamine lauryl sulfate;

alkylbenzene sulfonates, such as sodium dodecylbenzene sulfonate;

alkylnaphthalene sulfonates, such as sodium alkylnaphthalene sulfonate;

alkylsulfo succinates, such as sodium dialkylsulfo succinate;

alkyldiphenyl ether disulfonates, such as sodium alkyldiphenyl ether disulfonate;

alkyl phosphates, such as potassium alkyl phosphate;

polyoxy ethylene alkyl (or alkylallyl) sulfuric esters, such as sodium polyoxy ethylene lauryl ether sulfate, sodium polyoxy ethylene alkyl ether sulfate, triethanolamine polyoxy ethylene alkyl ether sulfate, and sodium polyoxy ethylene alkylphenyl ether sulfate;

anionic surfactants of special reacting type;

surfactants of special carboxylic acid type;

formalin condensates of naphthalene sulfonic acid, such as sodium salts of formalin condensates of β-naphthalene sulfonic acid, and sodium salts of formalin condensates of special aromatic sulfonic acid;

high molecular surfactants of special polycarboxylic acid type;

polyoxy ethylene alkyl phosphate; etc.

Also, examples of the nonionic surfactant include:

polyolefin oxides, such as polyethylene glycol, polypropylene glycol, and a polyethylene glycol—polypropylene glycol block copolymer;

polyoxy ethylene alkyl ethers, such as polyoxy ethylene lauryl ether, polyoxy ethylene cetyl ether, polyoxy ethylene stearyl ether, polyoxy ethylene oleyl ether, and polyoxy ethylene higher alcohol ether;

polyoxy ethylene alkyl aryl ethers, such as polyoxy ethylene nonylphenyl ether;

polyoxy ethylene derivatives;

sorbitan fatty acid esters, such as sorbitan monolaurate, sorbitan monopalmitate, sorbitan monostearate, sorbitan tristearate, sorbitan monooleate, sorbitan trioleate, sorbitan sesquiolate, and sorbitan distearate;

polyoxy ethylene sorbitan fatty acid esters, such as polyoxy ethylene sorbitan monolaurate, polyoxy ethylene sorbitan monopalmitate, polyoxy ethylene sorbitan monostearate, polyoxy ethylene sorbitan tristearate, polyoxy ethylene sorbitan monooleate, and polyoxy ethylene sorbitan trioleate;

polyoxy ethylene sorbitol fatty acid esters, such as polyoxy ethylene sorbit tetraoleate;

glycerine fatty acid esters, such as glycerol monostearate, glycerol monooleate, and self-emulsifying glycerol monostearate;

polyoxy ethylene fatty acid esters, such as polyethylene glycol monolaurate, polyethylene glycol monostearate, polyethylene glycol distearate, and polyethylene glycol monooleate;

polyoxy ethylene alkylamine;

polyoxy ethylene curing caster oil;

alkylalkanolamido; etc.

Further, examples of the cationic surfactants and ampholytic surfactant include:

alkylamine salts, such as coconut amine acetate and stearyl amine acetate;

quaternary ammonium salts, such as lauryl trimethyl ammonium chloride, stearyl trimethyl ammonium chloride, cetyl trimethyl ammonium chloride, distearyl dimethyl ammonium chloride, and alkylbenzyl dimethyl ammonium chloride;

alkylbetaines, such as laurylbetaine, stearyl betaine, and lauryl carboxymethyl hydroxy ethyl imidazolynium betaine;

amine oxides, such as lauryl dimethyl amine oxide; etc.

In addition to the aforementioned examples, a fluorine surfactant and a siloxane surfactant can be used.

Of all the examples, polypropylene glycol and a polyethylene glycol—polypropylene glycol block copolymer are more preferable than the others for the following reasons: an added amount is small; they do not deteriorate the physical properties of the surface-treated dried product (that is, absorbent resin); and they are safe when handled.

An added amount of the surfactant is preferably in a range between 0.001 and 10 parts by weight, and more preferably in a range between 0.01 and 5 parts by weight, and most preferably in a range between 0.1 and 2 parts by weight with respect to 100 parts by weight of the hydrogel. If an added amount is less than 0.001 part by weight, particles of the hydrogel agglomerate. On the other hand, if an added amount exceeds 10 parts by weight, the effect of adding the surfactant is not improved to meet an increased amount, and the physical properties of the absorbent resin obtained as the final product may be deteriorated.

As has been discussed, the manufacturing method of the absorbent resin of the present embodiment uses the non-agglomerating type dryer which dries the hydrogel with stirring in the drying step. When the non-agglomerating type dryer is used, the incompletely dried product can be efficiently separated from the dried product and inconveniences caused when the incompletely dried product is mixed into the dried product can be prevented like in Embodiment 1. Also, deterioration of the physical properties of the resulting absorbent resin can be reduced, thereby making it possible to manufacture the absorbent resin of a higher quality.

Further, it is particularly preferable to use a pneumatic dryer equipped with a pulverizer and a classifier as the dryer used in the hydrogel drying step. This is because, when such a pneumatic dryer is used, not only can a large volume of the hydrogel be treated continuously, but also the manufacturing process of the absorbent resin can be shortened considerably.

The absorbent resin pulverized in the above manner can be directly used as the product, but to further improve the absorbing ability, it is more preferable to crosslink the vicinity of the surface of the absorbent resin by a surface crosslinking agent having two or more functional groups reactive with functional groups of the absorbent resin, such as carboxyl groups. Examples of the crosslinking agent include:

polyhydroxy alcohols, such as ethylene glycol, 1,4-butanediol, 1,6-hexanediol, propylene glycol, and glycerine;

alkylene carbonate compounds, such as ethylene carbonate and propylene carbonate;

polyvalent epoxy compounds, such as (poly)ethylene glycol diglycidyl ether;

polyvalent amine compounds, such as ethylene diamine and polyethylene imine;

polyvalent metal compounds, such as aluminum sulfate, aluminum (poly)chloride; etc.

The absorbent resin obtained by the manufacturing method of the present invention attains excellent absorbing abilities, and for this reason, can be suitably used in diversified fields including:

sanitary goods (body-fluid absorbing goods), such as paper diapers, sanitary napkins, incontinence pads, wound protecting materials, and wound curing materials;

urine absorbing pads for pets;

civil construction materials, such as water-retaining materials for building materials or soil, water stopping materials, packing materials, and gel water-bags;

food-preserving materials, such as drip absorbing materials, freshness keeping materials, cold insulating materials;

industrial goods, such as water-oil separating materials, anti-dewing material, coagulating materials;

farming and gardening materials, such as water-retaining materials for plants and soil; etc.

The following will explain in detail the manufacturing method of the absorbent resin of the present invention by way of examples and comparative examples for purposes of explanation only, without any intention as a definition of the limits of the invention. In the following, "part(s)" means "part(s) by weight" and "%" means "wt %" unless specified otherwise.

Absorbing capacity and a soluble content of the absorbent resin were measured in the following manners.

(a) Absorbing Capacity

Here, an aqueous solution with a chemical make-up of 0.200% of sodium sulfate, 0.200% of potassium chloride, 0.050% of magnesium chloride hexahydrate, 0.025% of calcium chloride dihydrate, 0.085% of ammonium dihydrogenphosphate, 0.015% of diammonium hydrogenphosphate, and 99.425% of deionized water, namely, a synthetic urine, was prepared.

Then, 0.2 g of the absorbing agent was uniformly placed into a tea-bag sack (60 mm×60 mm) made of non-woven fabric and the tea-bag sack was dipped in the synthetic urine at room temperature for 30 minutes. Then, the tea-bag sack was taken out, and subjected to hydro-extraction for 3 minutes at 250 G using a centrifugal separator, after which the weight $W_1$ (g) of the tea-bag sack was measured. Further, the same process was repeated with an empty tea-bag sack, and the weight $W_0$ (g) of the empty tea-bag sack was measured. Absorbing capacity (g/g) was calculated using the weights $W_1$ and $W_0$ on the basis of the following equation:

$$\text{Absorbing Capacity (g/g)} = \frac{\text{Weight } W_1(g) - \text{Weight } W_0(g)}{\text{Weight of Absorbing Agent (g)}}.$$

(b) Soluble Content

After the absorbent resin was collected to obtain 0.5 g of solid, the absorbent resin was dispersed in 1 L of ion exchanged water. Then, the dispersed solution was kept stirred for 16 hours to let the same swell in a satisfactory manner. Subsequently, the dispersed solution was filtered through a filter paper, and the filtrate was titrated by a colloidal titration method. Then, from an amount of titration or the like, an amount of compounds produced by heat deterioration and dissolved in the filtrate, more specifically, an amount of water-soluble polyacrylic acid (polyacrylate), namely, a soluble content (%) was calculated. It is judged that, the greater the soluble content (an amount of water-soluble content), the more badly the absorbent resin is heat-deteriorated during the drying step.

EXAMPLE 1

Here, a monomer aqueous solution was prepared by mixing 39.3 parts of acrylic acid, 257.7 parts of 37% aqueous solution of sodium acrylate, 0.46 part of polyethylene glycol diacrylate (having 8 polyethylene glycol units in average), and 148.5 parts of water. Then, a nitrogen gas was blown into the monomer aqueous solution so as to remove residual dissolved oxygen. Subsequently, the monomer aqueous solution was placed in a two-arm type kneader with a jacket and a temperature of the monomer aqueous solution was kept at 25° C.

Then, the blades of the kneader was turned at a rate of 40 rpm under nitrogen gas flow while the polymerization reaction was started by adding 0.4 part of 20% aqueous solution of sodium persulfate, 1.6 part of 10% aqueous solution of 2,2'-azobis(2-amidinopropane)hydrochloride, 0.7 part of 0.1% aqueous solution of L-ascorbic acid, and 0.4 part of 0.35% aqueous solution of hydrogen peroxide as a polymerization initiator.

After the start of the polymerization was confirmed by the white suspension of the monomer aqueous solution, the blades were stopped when the temperature of the monomer aqueous solution (internal temperature) rose to 30° C. Then, the aqueous solution was allowed to stand with gradual heating by the jacket until the internal temperature rises to 60° C. When the internal temperature exceeded 60° C., the blades were turned again to divide the produced hydrogel to particles, while the polymerization was continued until the internal temperature rose to 77° C.

The hydrogel thus obtained was dried by the box-type dryer (FIG. 1) for 65 minutes at 160° C., after which the resulting plates of aggregates of hydrophilic hydrogel were disintegrated by a hammer, and sifted through a 10 mm-sieve. When the product remaining on the 10 mm-sieve was disintegrated by a cutting plier, inside of which was rubber hydrogel (incompletely dried product). The water content of the incompletely dried product was 30%.

On the other hand, the product passing through the 10 mm-sieve was pulverized by a roll mill having three pairs of rolls commercially known as GRANULATOR of Nippon Granulator Co., Ltd. (the gap of each roll is: 1.6 mm, 0.4 mm, and 0.15 mm from top to bottom). Since the incompletely dried product was not delivered to this pulverizing step, the product passing through the sieve were pulverized in a satisfactory manner. The pulverized product obtained in the above manner was classified with a 0.85 mm-sieve, whereby absorbent resin (1) of the present invention was obtained.

The dried absorbent resin (1) was high-grade absorbent resin with water content of 5%, absorbing capacity of 65 (g/g), and soluble content of 15%.

Comparative Example 1

Comparative Example 1 was conducted in the same manner as Example 1 except that the disintegrated hydrogel was not classified with a sieve, and pulverized directly by the 3-stage roll mill. Then, rubber of incompletely dried product adhered to the rolls.

EXAMPLE 2

A monomer aqueous solution containing 75%-neutralized sodium acrylate were neutralized, and 0.04 mol % (with respect to sodium acrylate) of polyethylene glycol diacrylate (having 8 ethylene oxide units in average) was prepared. Here, an amount of sodium acrylate was 35%. Then, nitrogen was blown into the monomer aqueous solution to reduce a concentration of residual dissolved oxygen therein to 0.1 ppm or less.

Then, 0.02 mol % of water-soluble azo initiator of Wako Pure Chemical Industries, Ltd, commercially known as V-50 (with respect to the monomer of acrylic acid), 0.002 g/mol of L-ascorbic acid (with respect to the monomer of sodium acrylate), and 0.001 g/mol of hydrogen peroxide (with respect to the monomer of sodium acrylate) were added to the monomer aqueous solution in this order to trigger the polymerization. The temperature of the monomer aqueous solution was 22° C. at the beginning of the polymerization, and rose to 82 ° C. 12 minutes later.

When the polymerization ended, the resulting hydrogel was cut into pieces of 25 mm cube by a Guillotine cutter. After 0.5% (with respect to solid) of a polyethylene glycol—polypropylene glycol block copolymer commercially known as ADK PULRONIC L44 of Asahi Denka Kogyo K.K. was added to the resulting angular hydrogel, the hydrogel was further divided by a cutting mill. An average particle size of the powdery hydrogel obtained by the above dividing was 2000 $\mu$m.

The resulting hydrogel was conveyed and dried with hot air of 225° C. at air flow of 20 m$^3$/min. by the pneumatic dryer (FIG. 12). The powdery hydrogel was pulverized by the stirrup-type pulverizer at a rate of 4000 rpm with drying, and the resulting pulverized product was classified by a pneumatic classifier, so that the dried product of a predetermined particle size was released from the dryer and the incompletely dried product was dried further.

Absorbent resin (2) of the present invention was obtained in the above manner. The dried absorbent resin (2) was high-grade absorbent resin with water content of 4%, absorbing capacity of 65 (g/g), and soluble content of 12%.

EXAMPLE 3

A monomer aqueous solution was prepared by mixing 155 parts of acrylic acid, 1636 parts of 37% aqueous solution of sodium acrylate, 0.5 part of trimethylol propane triacrylate, and 183 parts of water. Then, a nitrogen gas was blown into the monomer aqueous solution to remove residual dissolved oxygen therein. Subsequently, the monomer aqueous solution was placed in the two-arm type kneader with a jacket, and kept at a temperature of 25° C.

Then, as a polymerization initiator, 24 part of 5% of aqueous solution of sodium persulfate and 1.2 part of 0.5% aqueous solution of L-ascorbic acid were added to the monomer aqueous solution while the blades of the kneader was kept turned at 40 rpm under nitrogen gas flow, upon which the polymerization reaction was started with the monomer aqueous solution being suspended in white.

The polymerization reaction was continued while the blades were kept turned. Then, 10 minutes later, the temperature (internal temperature) of the monomer aqueous solution rose to 90° C. (polymerization peak temperature), whereupon the hydrogel was produced. Then, the blades was kept turned for 20 minutes more to pulverize the hydrogel thus obtained to particles.

The hydrogel thus obtained was dried by the box-type dryer (FIG. 1) for 65 minutes at 160° C., after which the resulting plates of aggregates of the hydrophilic hydrogel were disintegrated by a hammer, and sifted through a 10 mm-sieve. When the product remaining on the 10 mm-sieve was disintegrated by a cutting plier, inside of which was rubber hydrogel (incompletely dried product). The water content of the incompletely dried product was 25%.

On the other hand, the product passing through the 10 mm-sieve was pulverized by a 3-stage roll mill identical with the one used in Example 1. Since the incompletely dried product was not delivered to this pulverizing step, the product passing through the sieve were pulverized in a satisfactory manner. The pulverized product obtained in the above manner was classified with a 0.85 mm-sieve, whereby absorbent resin (3) of the present invention was obtained.

The dried absorbent resin (3) was high-grade absorbent resin with water content of 5%, absorbing capacity of 48 (g/g), and soluble content of 16%.

As has been discussed above, by adopting the manufacturing method of absorbent resin of the present invention, high-quality water absorbent resin were manufactured efficiently by avoiding inconveniences caused by the incompletely dried hydrogel.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A manufacturing method of absorbent resin comprising:

a drying step of drying hydrogel of a crosslinked polymer to obtain a product;

a pulverizing step of pulverizing said product; and a separating step performed when the product has a water content exceeding 15 wt. % as calculated by an equation $[(wt_0-wt_1/wt_0]\times 100$ where $wt_0$ is a weight of the hydrogel of the crosslinked polymer before it is dried, and $wt_1$ is a weight of the hydrogel of the crosslinked polymer after it has been dried for 3 hours at 180° C.

the separating step of separating incompletely dried material of said hydrogel of the crosslinked polymer from the product, said separating step being conducted one of before and during said pulverizing step.

2. The manufacturing method of absorbent resin of claim 1, wherein, in said separating step, said incompletely dried material is separated from said product by classifying said product.

3. The manufacturing method of absorbent resin of claim 1, wherein:

a dryer used in said drying step is a band dryer; and said manufacturing method further comprises a disintegrating step of disintegrating aggregates of said product, said disintegrating step being conducted one of before and during said separating step.

4. The manufacturing method of absorbent resin of claim 1, wherein, in said pulverizing step, said product is pulverized by a roll mill with at least one pair of rolls.

5. The manufacturing method of absorbent resin of claim 1, wherein a pneumatic dryer used in said drying step; and the pneumatic dryer is equipped with a pulverizer which pulverizes said hydrogel of a crosslinked polymer to a pulverized product, and a classifier which classifies said pulverized product.

6. A manufacturing method of absorbent resin comprising:

drying hydrogel of a crosslinked polymer to obtain a product;

pulverizing the product; and separating the product to separate more material from less material, the product being separated one of before and during pulverizing the product.

7. The manufacturing method of absorbent resin of claim 3, further comprising the step of coarse-pulverizing the aggregates disintegrated in the disintegrating step.

8. The manufacturing method of absorbent resin of claim 7, wherein the disintegrating step is carried out by applying pressure and the coarse-pulverizing step is carried out by a pin mill.

9. The manufacturing method of absorbent resin as set forth in claim 1, wherein the hydrogel of the crosslinked polymer is divided before the drying step to select particles to be dried, such that 90% or greater of the particles to be dried have a particle size ranging from 0.1 to 10 mm, the particles to be dried having an average particle size in a range of 0.5 to 5 mm.

10. The manufacturing method of absorbent resin of claim 1, wherein a dryer is used in the drying step, and the incompletely dried material separated in the separating step is fed back to the dryer used in the drying step, to redry the incompletely dried material.

11. The manufacturing method of absorbent resin of claim 1, wherein a dryer is used in the drying step, and the incompletely dried material separated in the separating step is redried in a dryer different from the dryer used in the drying step.

12. A manufacturing method of an absorbent resin comprising:

a drying step of drying hydrogel of a crosslinked polymer to obtain a product;

a pulverizing step of pulverizing said product; and a separating step which is selected from the group consisting of:

(a) when an agglomerating type dryer is used in the drying step, disintegrating aggregates of the product and then separating out those particles having a particle size exceeding 50 mm as an incompletely dried material; and (b) when a non-agglomerating type dryer is used in the drying step, separating the product so as to separate out those particles having a particle size exceeding 50 mm as incompletely dried material.

13. The manufacturing method of absorbent resin of claim 12, wherein step (a) is used as the separating step after disintegrating aggregates of the product, the aggregates are coarse-pulverized, and the product is separated after the aggregates of the product have been disintegrated and coarse-pulverized.

14. The manufacturing method of absorbent resin of claim 13, wherein the aggregates of the product are disintegrated by applying pressure, and the aggregates of the product are coarse-pulverized by a pin mill.

15. The manufacturing method of absorbent resin of claim 12, wherein step (a) is performed as the separating step, and a band dryer is used as the agglomerating type dryer.

16. The manufacturing method of absorbent resin of claim 12, wherein, in said pulverizing step, said product is pulverized by a roll mill with at least one pair of rolls.

17. The manufacturing method of absorbent resin of claim 12, wherein a pneumatic dryer used in said drying step; and the pneumatic dryer is equipped with a pulverizer which pulverizes said hydrogel of a crosslinked polymer to a pulverized product, and a classifier which classifies said pulverized product.

18. The manufacturing method of absorbent resin as set forth in claim 12, wherein the hydrogel of the crosslinked polymer is divided before the drying step to select particles to be dried such that 90% or greater of the particles to be dried have a particle size ranging from 0.1 to 10 mm, the particles to be dried having an average particle size in a range of 0.5 to 5 mm.

19. The manufacturing method of absorbent resin of claim 12, wherein a dryer is used in the drying step, and the incompletely dried material separated in the separating step is fed back to the dryer used in the drying step to redry the incompletely dried material.

20. The manufacturing method of absorbent resin of claim 12, wherein a dryer is used in the drying step, and the incompletely dried material separated in the separating step is redried in a dryer different from the dryer used in the drying step.

21. The manufacturing method of absorbent resin of claim 6, wherein material having a water content exceeding 15 wt. % is separated from the product as incompletely dried material, the water content being calculated by an equation $$[wt_0 - wt_1)/wt_0] \times 100$$

where $wt_0$ is a weight of the hydrogel of the crosslinked polymer before it is dried, and $wt_1$ is a weight of the hydrogel of the crosslinked polymer after it has been dried.

22. The manufacturing method of absorbent resin of claim 12, wherein step (b) is used as the separating step, and before separating the product, aggregates of the product are disintegrated.

23. A manufacturing method of an absorbent resin comprising:

a drying step of drying hydrogel of a crosslinked polymer to obtain a product;

a pulverizing step of pulverizing said product; and a separating step which is selected from the group consisting of:

(a) when an agglomerating type dryer is used in the drying step, disintegrating aggregates of the product and then separating out those particles having a particle size exceeding 5 mm as an incompletely dried material; and (b) when a non-agglomerating type dryer is used in the drying step, separating the product so as to separate out those particles having a particle size exceeding 5 mm as incompletely dried material.

24. The manufacturing method of absorbent resin of claim 23, wherein step (a) is used as the separating step, after disintegrating aggregates of the product, the aggregates are coarse-pulverized, and the product is separated after the aggregates of the product have been disintegrated and coarse-pulverized.

25. The manufacturing method of absorbent resin of claim 24, wherein the aggregates of the product are disintegrated by applying pressure, and the aggregates of the product are coarse-pulverized by a pin mill.

26. The manufacturing method of absorbent resin of claim 23, wherein step (a) is performed as the separating step, and a band dryer is used as the agglomerating type dryer.

27. The manufacturing method of absorbent resin of claim 23, wherein, in said pulverizing step, said product is pulverized by a roll mill with at least one pair of rolls.

28. The manufacturing method of absorbent resin of claim 23, wherein a pneumatic dryer used in said drying step; and the pneumatic dryer is equipped with a pulverizer which pulverizes said hydrogel of a crosslinked polymer to a pulverized product, and a classifier which classifies said pulverized product.

29. The manufacturing method of absorbent resin as set forth in claim 23, wherein the hydrogel of the crosslinked polymer is divided before the drying step to select particles to be dried such that 90% or greater of the particles to be dried have a particle size ranging from 0.1 to 10 mm, the particles to be dried having an average particle size in a range of 0.5 to 5 mm.

30. The manufacturing method of absorbent resin of claim 23, wherein a dryer is used in the drying step, and the incompletely dried material separated in the separating step is fed back to the dryer used in the drying step to redry the incompletely dried material.

31. The manufacturing method of absorbent resin of claim 23, wherein a dryer is used in the drying step, and the incompletely dried material separated in the separating step is redried in a dryer different from the dryer used in the drying step.

32. The manufacturing method of absorbent resin of claim 23, wherein step (b) is used as the separating step, and before separating the product, aggregates of the product are disintegrated.

* * * * *

UNITED STATES PATENT AND TRADEMARK OFFICE
CERTIFICATE OF CORRECTION

PATENT NO.    : 6,291,636 B1
DATED         : September 18, 2001
INVENTOR(S)   : Koji Miyake et al.

It is certified that error appears in the above-identified patent and that said Letters Patent is hereby corrected as shown below:

Column 17,
Line 17, insert -- . -- after "step)"

Column 21,
Line 17, change "fan4" to -- fan44 --.

Column 28,
Line 51, change "1 L" to -- 1L --.

Column 30,
Line 5, change "0.001 g/mol" to -- 0.001g/mol --.

Column 31,
Line 36, insert -- , -- after "C.".

Signed and Sealed this

Second Day of April, 2002

*Attest:*

*Attesting Officer*

JAMES E. ROGAN
*Director of the United States Patent and Trademark Office*